(12) United States Patent
Bastian et al.

(10) Patent No.: US 8,404,687 B2
(45) Date of Patent: Mar. 26, 2013

(54) DISUBSTITUTED PHTHALAZINE HEDGEHOG PATHWAY ANTAGONISTS

(75) Inventors: Jolie Anne Bastian, Indianapolis, IN (US); Philip Arthur Hipskind, New Palestine, IN (US); Daniel Jon Sall, Greenwood, IN (US); Takako Wilson (nee Takakuwa), Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/122,212

(22) PCT Filed: Oct. 22, 2009

(86) PCT No.: PCT/US2009/061573
§ 371 (c)(1),
(2), (4) Date: Apr. 1, 2011

(87) PCT Pub. No.: WO2010/062507
PCT Pub. Date: Jun. 3, 2010

(65) Prior Publication Data
US 2011/0190304 A1    Aug. 4, 2011

Related U.S. Application Data

(60) Provisional application No. 61/110,703, filed on Nov. 3, 2008.

(51) Int. Cl.
*A01N 43/58* (2006.01)
*A01N 43/60* (2006.01)
*A61K 31/495* (2006.01)
*C07D 237/30* (2006.01)

(52) U.S. Cl. .................................... 514/248; 544/237

(58) Field of Classification Search ............... 514/248; 544/237
See application file for complete search history.

(56) References Cited

U.S. PATENT DOCUMENTS

| | | | |
|---|---|---|---|
| 3,753,988 | A | 8/1973 | Rodway et al. |
| 5,985,878 | A | 11/1999 | Stokbroekx et al. |
| 6,432,970 | B2 | 8/2002 | Beachy et al. |
| 2009/0048259 | A1 | 2/2009 | Austin et al. |
| 2010/0324048 | A1 | 12/2010 | Hipskind |
| 2011/0046143 | A1 | 2/2011 | Hipskind |

FOREIGN PATENT DOCUMENTS

| | | |
|---|---|---|
| WO | WO 97/26258 A1 | 7/1997 |
| WO | WO 99/52534 A1 | 10/1999 |
| WO | WO 00/74706 A1 | 12/2000 |
| WO | WO 03/088970 A2 | 10/2003 |
| WO | WO 2004/020599 A2 | 3/2004 |
| WO | 2005/033288 A2 | 4/2005 |
| WO | WO 2005/080378 A1 | 9/2005 |
| WO | WO 2006/004589 A2 | 1/2006 |
| WO | WO 2006/028958 A2 | 3/2006 |
| WO | WO 2008/028689 A1 | 3/2008 |
| WO | WO 2008/110611 A1 | 9/2008 |
| WO | WO 2009/002469 A1 | 12/2008 |
| WO | WO 2009/035568 A1 | 3/2009 |
| WO | WO 2009/134574 A2 | 11/2009 |
| WO | WO 2010/007120 A1 | 1/2010 |
| WO | WO 2010/056588 A1 | 5/2010 |
| WO | WO 2010/056620 A1 | 5/2010 |

OTHER PUBLICATIONS

Pinedo et al (2000) NcNagib et al (2000).*
Frank-Kamenetsky, M., et al., "Small-molecular modulators of Hedgehog signaling: identification and characterization of Smoothened agonists and antagonists," Journal of Biolology vol. 1, Issue 2, Article 10, pp. 10.1-10.19 (2002).
Lee, J., et al., "A small-muleclar antagonist of the Hedgehog signaling pathway," ChemBioChem, vol. 8, pp. 1916-1919 (2007).
McMahon, G., VEGF Receptor Signaling in Turnor Angiogenisis. The Oncologist, 5(suppl 1):3-10 (2000). [www.TheOncologist.com].
Pinedo, et al., "Translational Research . . . ," The Oncologist, 5(suppl1):1-2 [www.TheOncologist.com], (2000).
Tremblay, M., et al., "Semisynthetic cyclopamine analogues as potent and orally bioavailable Hedgehog pathway antagonists," J. Med. Chem., vol. 51, pp. 6646-6649 (2008).
Tremblay, M., et al., "Recent patents for Hedgehog pathway inhibitors for the treatment of malignancy," Expert Opin. Ther. Patents 19(8):1039-1056 (2009).

* cited by examiner

*Primary Examiner* — Paul V. Ward
(74) *Attorney, Agent, or Firm* — Danica Hostettler; John C. Demeter

(57) ABSTRACT

The present invention provides novel 1,4-disubstituted phthalazine hedgehog pathway antagonists useful in the treatment of cancer.

(I)

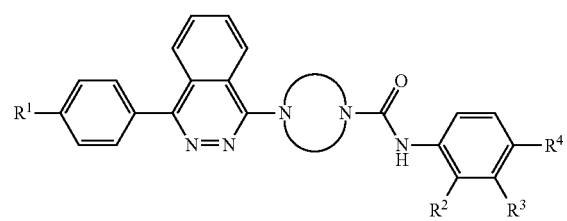

13 Claims, No Drawings

DISUBSTITUTED PHTHALAZINE HEDGEHOG PATHWAY ANTAGONISTS

This application is a national phase application under 35 U.S.C. Section 371 of PCT/US2009/061573, filed Oct. 22, 2009, which claims the benefit under 35 U.S.C. Section 119(e) of U.S. provisional patent application 61/110,703, filed Nov. 3, 2008.

The present invention relates to Hedgehog pathway antagonists and, more specifically, to novel 1,4-disubstituted phthalazines and therapeutic use thereof. The Hedgehog (Hh) signaling pathway plays an important role in embryonic pattern formation and adult tissue maintenance by directing cell differentiation and proliferation. The Hedgehog (Hh) protein family, which includes Sonic Hedgehog (Shh), Indian Hedgehog (Ihh), and Desert Hedgehog (Dhh) are secreted glycoproteins that undergo post-translational modifications, including autocatalytic cleavage and coupling of cholesterol to the amino-terminal peptide to form the fragment that possesses signaling activity. Hh binds to the twelve-pass transmembrane protein Ptch (Ptch1 and Ptch2), thereby alleviating Ptch-mediated suppression of Smoothened (Smo). Smo activation triggers a series of intracellular events culminating in the stabilization of the Gli transcription factors (Gli1, Gli2, and Gli3) and the expression of Gli-dependent genes that are responsible for cell proliferation, cell survival, angiogenesis and invasion.

Hh signaling has recently attracted considerable interest based on the discovery that aberrant activation of Shh signaling leads to the formation of various tumors, e.g., pancreatic cancer, medulloblastoma, basal cell carcinoma, small cell lung cancer, and prostate cancer. Several Hh antagonists have been reported in the art, such as the steroidal alkaloid compound IP-609; the aminoproline compound CUR61414; and the 2,4-disubstituted thiazole compound JK18. WO2005033288 discloses certain 1,4-disubstituted phthalazine compounds asserted to be hedgehog antagonists. Similarly, WO2008110611 discloses certain 1,4 disubstituted phthalazine compounds related to the diagnosis and treatment of pathologies related to the hedgehog pathway.

There still exists a need for potent hedgehog pathway inhibitors, particularly those having desirable pharmacodynamic, pharmacokinetic and toxicology profiles. The present invention provides novel 1,4-disubstituted phthalazines that are potent antagonists of this pathway.

The present invention provides a compound of Formula I:

Formula I

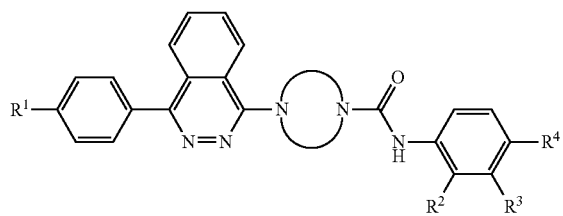

wherein,
$R^1$ is hydrogen, fluoro, cyano, trifluoromethyl or methoxy;
$R^2$ is hydrogen, fluoro or trifluoromethyl;
$R^3$ is hydrogen or chloro, provided that at least one of $R^2$ and $R^3$ is hydrogen;
$R^4$ is chloro, fluoro, cyano, trifluoromethyl, methoxy, difluoromethoxy or trifluoromethoxy;

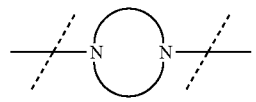

represents a substituted piperazine-1,4-diyl selected from the group consisting of

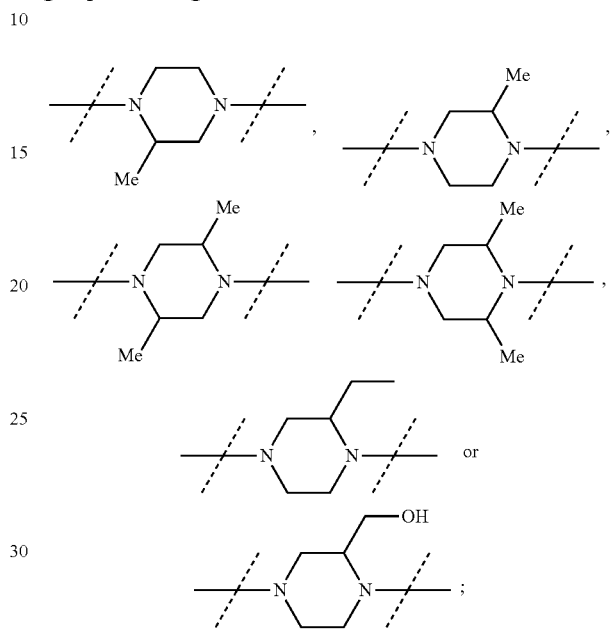

or a pharmaceutically acceptable salt thereof.

In the piperazine ring structures above it will be understood that the left side of the piperazine ring, as drawn, is linked to the bicyclic phthalizine and the right side of the piperazine ring is linked to the carbonyl.

It will be understood by the skilled artisan that the compounds of the present invention comprise a tertiary amine moiety and are capable of reaction with a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts, "*Journal of Pharmaceutical Sciences*, Vol 66, No. 1, January 1977.

Specific embodiments of the invention include compounds of Formula I, or a pharmaceutically acceptable salt thereof, wherein:
(a) $R^1$ is hydrogen, fluoro or cyano;
(b) $R^1$ is fluoro;
(c) $R^2$ is hydrogen or fluoro;
(d) $R^2$ is hydrogen;
(e) $R^3$ is hydrogen;
(f) $R^4$ is fluoro, chloro, cyano, trifluoromethoxy, difluoromethoxy or trifluoromethyl;
(g) $R^4$ is fluoro or cyano;
(h) $R^4$ is fluoro;

(i)

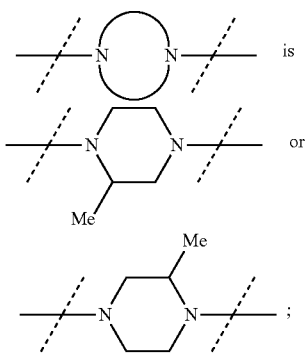

(j)

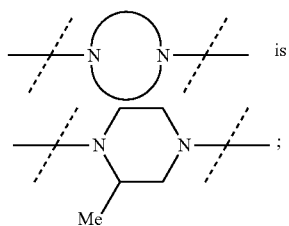

(k)

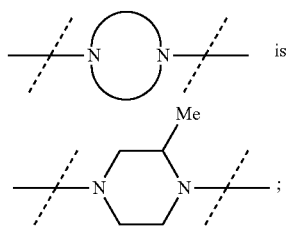

(l) $R^1$ is hydrogen, fluoro or cyano; and $R^2$ is hydrogen or fluoro;
(m) $R^1$ is hydrogen, fluoro or cyano; and $R^2$ is hydrogen;
(n) $R^1$ is fluoro; and $R^2$ is hydrogen or fluoro;
(o) $R^1$ is fluoro; and $R^2$ is hydrogen;
(p) $R^1$ is hydrogen, fluoro or cyano; $R^2$ is hydrogen or fluoro; and $R^4$ is fluoro, chloro, cyano, trifluoromethoxy, difluoromethoxy or trifluoromethyl;
(q) $R^1$ is hydrogen, fluoro or cyano; $R^2$ is hydrogen; and $R^4$ is fluoro, chloro, cyano, trifluoromethoxy, difluoromethoxy or trifluoromethyl;
(r) $R^1$ is fluoro; $R^2$ is hydrogen or fluoro; and $R^4$ is fluoro, chloro, cyano, trifluoromethoxy, difluoromethoxy or trifluoromethyl;
(s) $R^1$ is fluoro; $R^2$ is hydrogen; and $R^4$ is fluoro, chloro, cyano, trifluoromethoxy, difluoromethoxy or trifluoromethyl;
(t) $R^1$ is hydrogen, fluoro or cyano; $R^2$ is hydrogen or fluoro; $R^3$ is hydrogen; and $R^4$ is fluoro, chloro, cyano, trifluoromethoxy, difluoromethoxy or trifluoromethyl;
(u) $R^1$ is hydrogen, fluoro or cyano; $R^2$ is hydrogen; $R^3$ is hydrogen; and $R^4$ is fluoro, chloro, cyano, trifluoromethoxy, difluoromethoxy or trifluoromethyl;
(v) $R^1$ is fluoro; $R^2$ is hydrogen or fluoro; $R^3$ is hydrogen; and $R^4$ is fluoro, chloro, cyano, trifluoromethoxy, difluoromethoxy or trifluoromethyl; and
(w) $R^1$ is fluoro; $R^2$ is hydrogen; $R^3$ is hydrogen; and $R^4$ is fluoro, chloro, cyano, trifluoromethoxy, difluoromethoxy or trifluoromethyl;
(x) $R^1$ is fluoro; $R^2$ is hydrogen; $R^3$ is hydrogen; and $R^4$ is fluoro;
(y) $R^1$ is hydrogen, fluoro or cyano; $R^2$ is hydrogen or fluoro; and

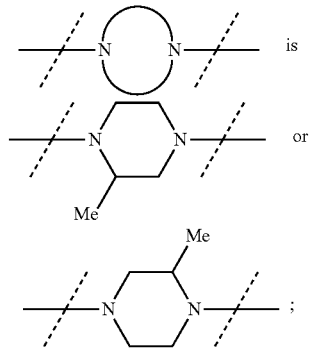

(z) $R^1$ is hydrogen, fluoro or cyano; $R^2$ is hydrogen; and

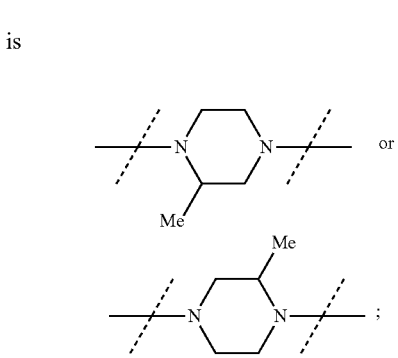

(z) $R^1$ is fluoro; $R^2$ is hydrogen or fluoro; and

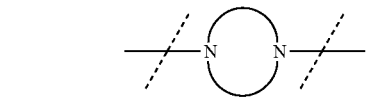

is

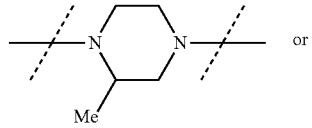

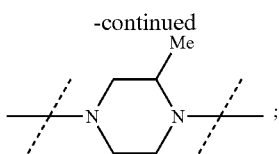

(aa) R¹ is hydrogen, fluoro or cyano; R² is hydrogen or fluoro; R³ is hydrogen; R⁴ is fluoro, chloro, cyano, trifluoromethoxy, difluoromethoxy or trifluoromethyl; and

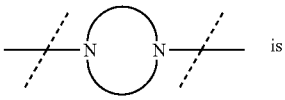 is

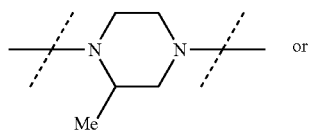 or

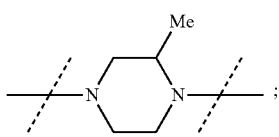 ;

(bb) R¹ is hydrogen, fluoro or cyano; R² is hydrogen; R³ is hydrogen; R⁴ is fluoro or cyano; and

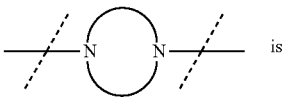 is

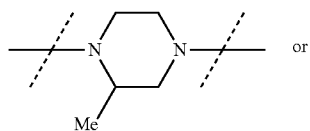 or

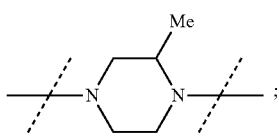 ;

The present invention also provides a pharmaceutical composition comprising a compound of Formula I, or a pharmaceutically acceptable salt thereof, in combination with a pharmaceutically acceptable excipient, carrier or diluent.

The compounds of the present invention are preferably formulated as pharmaceutical compositions administered by a variety of routes. Preferably, such compositions are for oral or intravenous administration. Such pharmaceutical compositions and processes for preparing them are well known in the art. See, e.g., REMINGTON: THE SCIENCE AND PRACTICE OF PHARMACY (A. Gennaro, et al., eds., 19th ed., Mack Publishing Co., 1995).

The present invention also provides a method of treating brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma in a patient comprising administering to a patient in need of such treatment an effective amount of a compound of Formula I, or a pharmaceutically acceptable salt thereof.

It will be understood that the amount of the compound actually administered will be determined by a physician under the relevant circumstances, including the condition to be treated, the chosen route of administration, the actual compound or compounds administered, the age, weight, and response of the individual patient, and the severity of the patient's symptoms. Dosages per day normally fall within the range of about 0.1 to about 5 mg/kg of body weight. In some instances dosage levels below the lower limit of the aforesaid range may be more than adequate, while in other cases still larger doses may be employed. Therefore, the above dosage range is not intended to limit the scope of the invention in any way. This invention also provides a compound of Formula I, or a pharmaceutically acceptable salt thereof, for use as a medicament.

Additionally, this invention provides use of a compound of Formula I, or a pharmaceutically acceptable salt thereof, in the manufacture of a medicament for treating cancer. In particular, the cancer is selected from the group consisting of brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer and melanoma.

Furthermore, this invention provides a pharmaceutical composition comprising a compound of Formula I, or a pharmaceutically acceptable salt thereof, as an active ingredient for treating brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma.

The compounds of Formula I, or salts thereof, may be prepared by a variety of procedures known in the art, as well as those described in the Schemes, Preparations, and Examples below. The specific synthetic steps for each of the routes described may be combined in different ways, or in conjunction with steps from different schemes, to prepare compounds of Formula I, or salts thereof.

The substituents, unless otherwise indicated, are as previously defined. The reagents and starting materials are generally readily available to one of ordinary skill in the art. Others may be made by standard techniques of organic and heterocyclic chemistry, techniques which are analogous to the syntheses of known structurally-similar compounds, and the procedures described in the Preparations and Examples which follow including any novel procedures.

As used herein, the following terms have the meanings indicated: "Et₂O" refers to diethyl ether; "DMF" refers to dimethylformamide; "DMSO" refers to dimethylsulfoxide; "EtOAc" refers to ethyl acetate; "THF" refers to tetrahydrofuran; "MeOH" refers to methanol; "MTBE" refers to methyl-tert-butyl ether; "boc" or "t-boc" refers to tert-butoxy carbonyl; "SCX" refers to strong cation exchange; and "IC₅₀" refers to the concentration of an agent that produces 50% of the maximal inhibitory response possible for that agent.

Scheme 1

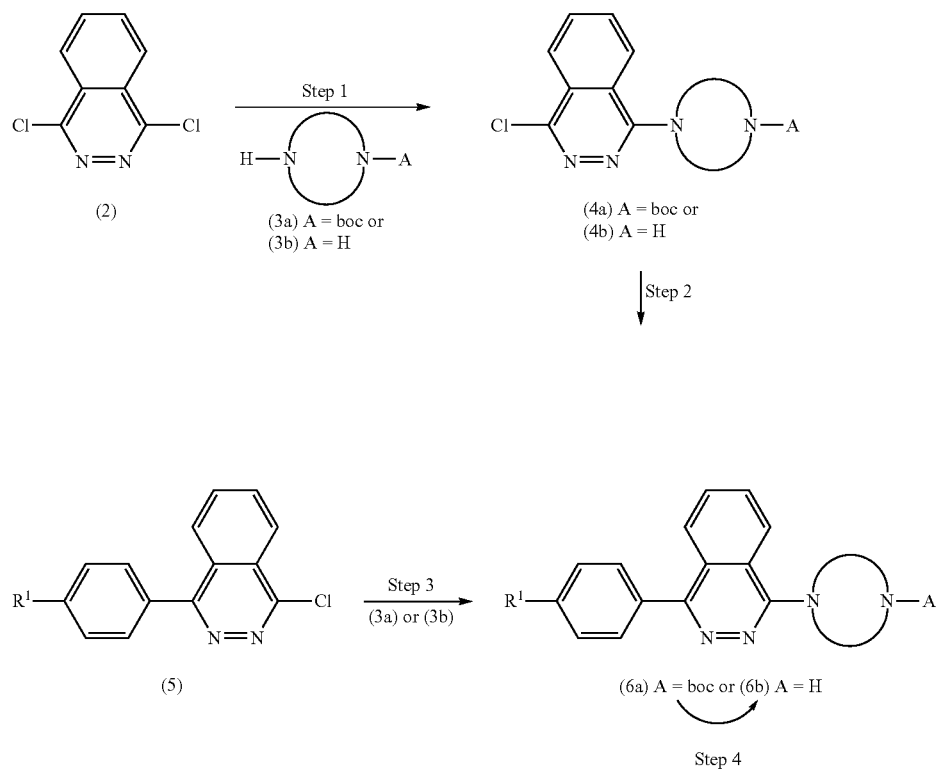

A compound of Formula (6b) can be prepared in accordance with reactions as depicted in Scheme 1.

In Scheme 1, Step 1, 1,4-dichlorophthalazine (2) can be reacted with a substituted piperazine (3a) or (3b) in a nucleophilic aromatic substitution (SNAr) to provide a piperazinyl phthalazine of formula (4a) or (4b). The reaction takes place in a dipolar aprotic solvent such as DMSO or DMF with an appropriate base such as triethylamine, diisopropylethylamine, or potassium carbonate. The mixture is heated at about 70-150° C. The skilled artisan will recognize that in some instances it will be advantageous to use a protecting group such as a t-boc group in a piperazine of formula (3a) allowing protection of the less hindered nitrogen atom, as in (S)-tert-butyl-3-methylpiperazine-1-carboxylate. Conversely, when reaction takes place at the less hindered nitrogen it may be possible to use unprotected piperazines such as cis-2,6-dimethylpiperazine or piperazin-2-yl-methanol. Neither is protection required when using 2,5-dimethylpiperazine.

In Step 2, the phthalazinyl chloride of formula (4) is reacted with a phenylboronic acid under Suzuki cross-coupling conditions. The skilled artisan will recognize that there are a variety of conditions useful for facilitating such cross-coupling reactions. The reaction conditions make use of a suitable solvent such as dioxane or dioxane/water. The reaction is accomplished in the presence of a base such as cesium carbonate or cesium fluoride. The reaction takes place in the presence of a palladium catalyst such as bis (di-tert-butyl(4-dimethylaminophenyl)phosphine)dichloropalladium(II), (1,1'-bis(diphenylphosphino)ferrocene)palladium(II) chloride, or (SP-4-1)-bis[bis(1,1-dimethylethyl)(4-methoxyphenyl)phosphine-κP]dichloro-palladium (prepared according to the synthesis of catalyst D in *J. Org. Chem.* 2007, 72, 5104-5112) under an inert atmosphere at a temperature of about 80-110° C. to give a phenyl piperazinyl phthalazine of formula (6a) or (6b).

Alternatively, in Step 3, a phenyl phthalazinyl chloride of formula (5) is reacted with a piperazine of formula (3 a) or (3b) in a nucleophilic aromatic substitution (SNAr) similar to that described in Step 1, above.

In Scheme 1, Step 4, amine functionality, such as that present in the phenyl piperazinyl phthalazine of formula (6a), can be deprotected to (6b) and further reacted to give compounds of the invention. Methods for removing nitrogen protecting groups are well known in the art (see, e.g., Greene and Wuts, *Protective Groups in Organic Synthesis*, 3$^{rd}$ Ed., John Wiley and Sons, New York, (1999)). For example, boc deprotection of the phenyl piperazinyl phthalazine of formula (6) can be accomplished under acidic conditions, such as with hydrogen chloride. The resulting HCl salt can be transformed to the free amine using an SCX column or an inorganic base such as sodium bicarbonate.

It will be appreciated by the skilled artisan that compounds of formula (5) in Scheme 1 are commercially available or can be readily prepared by methods similar to those described herein or by using procedures that are established in the art. For example, a 2-phenylcarbonyl benzoic acid, generated from a Grignard reaction of a phenyl magnesium bromide with phthalic anhydride, can be cyclized with hydrazine to give a 4-phenyl-2H-phthalazin-1-one. Subsequent treatment with phosphorous oxychloride provides the 1-chloro-4-phenyl-phthalazine of formula (5). Alternatively, 1,4-dichlorophthalazine can be reacted with a phenyl boronic acid in a Suzuki cross-coupling reaction to give the corresponding 1-chloro-4-phenyl-phthalazine of formula (5).

Scheme 2

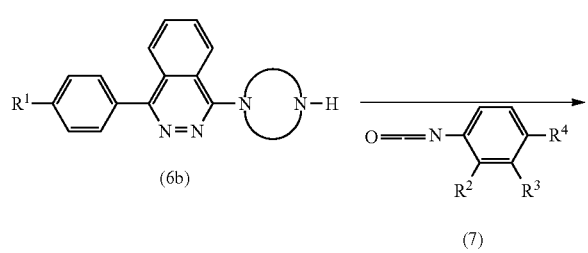

PREPARATION 1

(S)-tert-Butyl 4-(4-(4-fluorophenyl)phthalazin-1-yl)-2-methylpiperazine-1-carboxylate

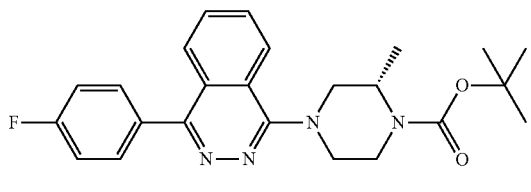 [SMILES: C[C@H]1CN(c2nnc(-c3ccc(F)cc3)c3ccccc23)CCN1C(=O)OC(C)(C)C]

Heat a mixture of 1-chloro-4-(4-fluorophenyl)phthalazine (5.0 g, 19.3 mmol), (S)-tert-butyl 2-methylpiperazine-1-carboxylate (5.03 g, 25.1 mmol) and triethylamine (8.1 mL, 59.0 mmol) in DMSO (97 mL) at 115° C. for 3 d. Pour the reaction mixture into water, rinsing with $CH_2Cl_2$. Extract with $Et_2O$. Wash the organic layer with water (2×), then dry over $Na_2SO_4$ and concentrate under reduced pressure. Purify the resulting residue by flash silica gel chromatography (gradient of 0 to 20% EtOAc in $CH_2Cl_2$) to provide the title compound as a pale yellow foam (7.05 g, 84%). ES/MS m/z 423.2 (M+1).

Alternate Procedure:

Add (S)-tert-butyl 2-methylpiperazine-1-carboxylate (276 g, 1.38 mol) to a slurry of 1-chloro-4-(4-fluorophenyl)phthalazine (275 g, 1.06 mol) and diisopropylethylamine (346 mL, 1.99 mol) in DMSO (2.56 L) at 25° C. Heat the mixture to 102° C. for 9 h. Cool the reaction to 25° C. and stir for 48 h. Add the mixture to EtOAc (2.5 L) and water (3.5 L). Extract the aqueous phase with ethyl acetate (2×2.0 L). Combine the organic layers, wash with water (2.5 L) and concentrate to a brown foam. Dissolve the foam in acetonitrile (1.0 L) and cool to 1° C. for 30 min. Filter the precipitate to obtain a tan solid. Concentrate the mother liquor and slurry the residue in acetonitrile (500 mL) for 30 min. Filter the mixture to obtain a tan solid. Combine the solid precipitates and dry in a vacuum oven (14 torr, 25° C.) for 25 h to obtain the title compound as a tan solid (435 g, 96%). ES/MS m/z 423.0 (M+1).

Prepare the piperazinylphthalazines in the table below by essentially following the procedure described in Preparation 1, using 1.5 eq of the appropriately substituted piperazine and 3-5 eq of triethylamine at a temperature of 115 to 150° C. for 3 to 6 days.

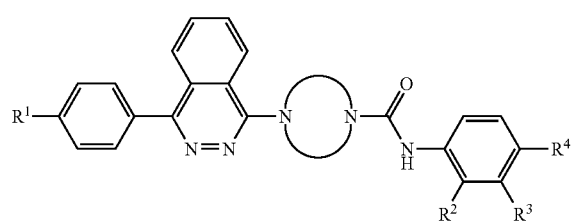

Formula I

In Scheme 2, the deprotected piperazinyl phthalazine of formula (6b) can be acylated using a substituted phenyl isocyanate in an inert solvent such as dichloromethane to give a urea of Formula (I).

The following Preparations and Examples are provided to illustrate the invention in further detail and represent typical synthesis of the compounds of Formula (I). The names of the compounds of the present invention are generally provided by ChemDraw Ultra® 10.0.

| Prep. No. | Chemical name | Structure | LC-ES/MS m/z |
|---|---|---|---|
| 2 | (S)-tert-Butyl 4-(4-(4-fluorophenyl)phthalazin-1-yl)-3-methylpiperazine-1-carboxylate | 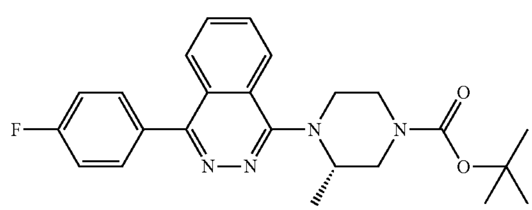 [SMILES: C[C@H]1CN(C(=O)OC(C)(C)C)CCN1c1nnc(-c2ccc(F)cc2)c2ccccc12] | 423.2 (M + 1) |
| 3 | (R)-tert-Butyl 4-(4-(4-fluorophenyl)phthalazin-1-yl)-2-methylpiperazine-1-carboxylate | 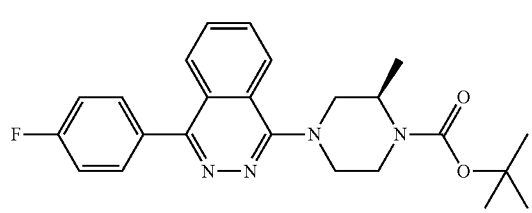 [SMILES: C[C@@H]1CN(c2nnc(-c3ccc(F)cc3)c3ccccc23)CCN1C(=O)OC(C)(C)C] | 423.2 (M + 1) |

| Prep. No. | Chemical name | Structure | LC-ES/MS m/z |
|---|---|---|---|
| 4* | (R)-tert-Butyl 4-(4-(4-fluorophenyl)phthalazin-1-yl)-3-methylpiperazine-1-carboxylate | 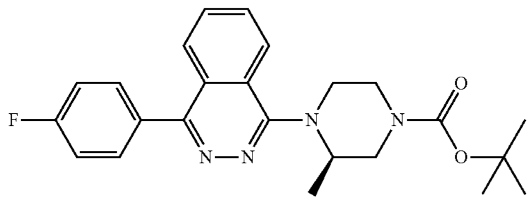 [SMILES: C[C@@H]1CN(C(=O)OC(C)(C)C)CCN1c1nnc(-c2ccc(F)cc2)c2ccccc12] | 423.2 (M + 1) |
| 5 | tert-Butyl 4-(4-(4-fluorophenyl)phthalazin-1-yl)-2-methylpiperazine-1-carboxylate | 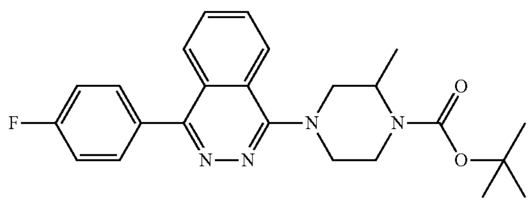 [SMILES: CC1CN(c2nnc(-c3ccc(F)cc3)c3ccccc23)CCN1C(=O)OC(C)(C)C] | 423.0 (M + 1) |
| 6 | tert-Butyl 4-(4-(4-fluorophenyl)phthalazin-1-yl)-3-methylpiperazine-1-carboxylate | 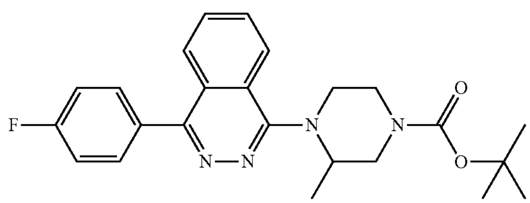 [SMILES: CC1CN(C(=O)OC(C)(C)C)CCN1c1nnc(-c2ccc(F)cc2)c2ccccc12] | 423.0 (M + 1) |

*Use DMF as solvent.

Alternate Procedure for Preparation 2:

Add 1-chloro-4-(4-fluorophenyl)phthalazine (200 g, 773 mmol) to a solution of (S)-tert-butyl 3-methylpiperazine-1-carboxylate (232 g, 1.16 mol), diisopropylethylamine (674 mL, 28.1 mol), and DMSO (2.0 L). Heat the mixture to 120° C. for 60 h. Cool the mixture to 25° C., pour into ice water (3.0 L) and filter. Collect the solids, dissolve in $CH_2Cl_2$ (2.0 L), and extract with water (2.0 L). Concentrate the organic phase and add to a silica plug (3.0 kg silica) eluting with 3% THF in $CH_2Cl_2$ to yield the title compound as a yellow foam (126 g, 38%). ES/MS m/z 423.0 (M+1).

PREPARATION 7

(S)-tert-Butyl 2-ethyl-4-(4-(4-fluorophenyl)phthalazin-1-yl)piperazine-1-carboxylate

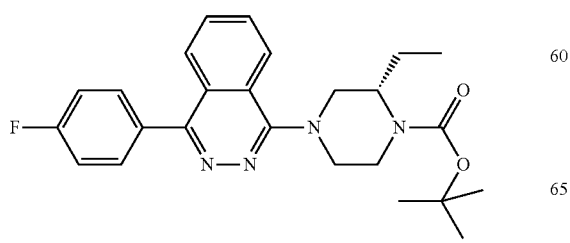

Heat a mixture of 1-chloro-4-(4-fluorophenyl)phthalazine (5.02 g, 19.4 mmol), (S)-tert-butyl 2-ethylpiperazine-1-carboxylate (5.00 g, 23.3 mmol) and $K_2CO_3$ (5.38 g, 38.9 mmol) in DMSO (75 mL) at 120° C. for 1 d. Pour the reaction mixture into water, rinsing with EtOAc. Extract with EtOAc. Wash the organic layer with water (2×), then brine, dry over $Na_2SO_4$, and concentrate under reduced pressure. Purify the resulting residue by flash silica gel chromatography (gradient of 20 to 80% EtOAc in hexanes) to provide the title compound (5.11 g, 60%). ES/MS m/z 437.2 (M+1).

Prepare the piperazinylphthalazine in the table below by essentially following the procedure described in Preparation 7, using cis-2,6-dimethylpiperazine.

| Prep. No. | Chemical name | Structure | ES/MS m/z |
|---|---|---|---|
| 8 | 1-(cis-3,5-Dimethylpiperazin-1-yl)-4-(4-fluorophenyl)phthalazine | 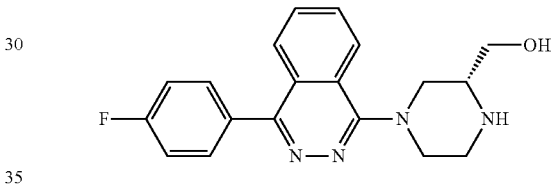 | 337.2 (M + 1) |

PREPARATION 9

(R)-(4-(4-(4-Fluorophenyl)phthalazin-1-yl)piperazin-2-yl)methanol

Dissolve 1-chloro-4-(4-fluorophenyl)phthalazine (0.1 g, 0.39 mmol), (R)-piperazin-2-ylmethanol (0.07 g, 0.58 mmol) and diisopropylethylamine (0.34 mL, 1.93 mmol) in DMSO (1 mL). Stir the reaction at 120° C. for 64 h. Purify the reaction mixture by flash silica gel chromatography (0-10% 2 M ammonia/MeOH in $CH_2Cl_2$) to yield the title compound as a brown solid (0.11 g, 84%). ES/MS m/z 339.0 (M+1).

Prepare the piperazinylphthalazines in the table below by essentially following the procedure described in Preparation 9, using the appropriately substituted piperazine.

| Prep. No. | Chemical name | Structure | ES/MS m/z |
|---|---|---|---|
| 10 | (S)-(4-(4-(4-Fluorophenyl)phthalazin-1-yl)piperazin-2-yl)methanol | 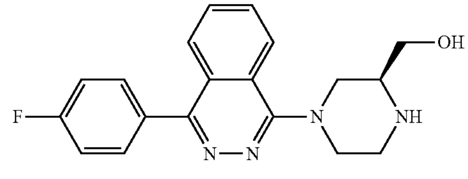 [SMILES: OC[C@@H]1CN(c2nnc(-c3ccc(F)cc3)c3ccccc23)CCN1] | 339.0 (M + 1) |
| 11 | 1-((2S,5S)-2,5-Dimethylpiperazin-1-yl)-4-(4-fluorophenyl)phthalazine | 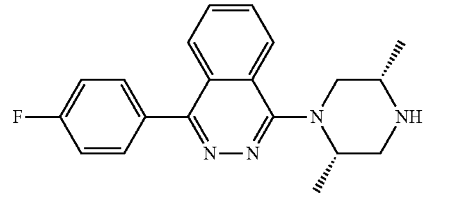 | 337.0 (M + 1) |

-continued

| Prep. No. | Chemical name | Structure | ES/MS m/z |
|---|---|---|---|
| 12 | 1-(cis-2,5-Dimethylpiperazin-1-yl)-4-(4-fluorophenyl)phthalazine (racemic mixture) | | 337.0 (M + 1) |
| 13 | 1-(trans-2,5-Dimethylpiperazin-1-yl)-4-(4-fluorophenyl)phthalazine (racemic mixture) | | 337.0 (M + 1) |

PREPARATION 14

(S)-tert-Butyl 4-(4-chlorophthalazin-1-yl)-3-methylpiperazine-1-carboxylate

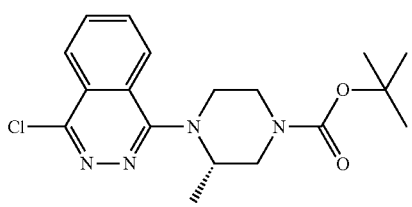 [SMILES: C[C@H]1CN(C(=O)OC(C)(C)C)CCN1c1nnc(Cl)c2ccccc12]

Heat a mixture of 1,4-dichlorophthalazine (10.0 g, 50.2 mmol), (S)-tert-butyl 3-methylpiperazine-1-carboxylate (15.1 g, 75.4 mmol) and triethylamine (21.0 mL, 150.7 mmol) in DMSO (200 mL) at 120° C. for 2 d. Pour the reaction mixture into water, rinsing with CH$_2$Cl$_2$. Extract with Et$_2$O. Wash the organic layer with water (2×), dry over Na$_2$SO$_4$, and concentrate under reduced pressure. Purify the resulting residue by flash silica gel chromatography (gradient of 0 to 20% EtOAc in CH$_2$Cl$_2$) to provide the title compound as a pale yellow solid (6.0 g, 33%). ES/MS m/z ($^{35}$Cl) 363.0 (M+1).

PREPARATION 15

(S)-tert-Butyl 4-(4-chlorophthalazin-1-yl)-2-methylpiperazine-1-carboxylate

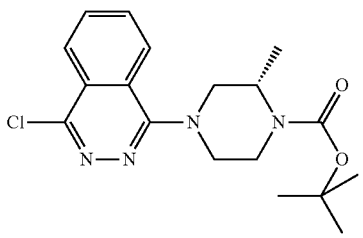 [SMILES: C[C@H]1CN(c2nnc(Cl)c3ccccc23)CCN1C(=O)OC(C)(C)C]

Heat a mixture of 1,4-dichlorophthalazine (7.80 g, 39.2 mmol), (S)-tert-butyl 2-methylpiperazine-1-carboxylate (4.98 g, 24.9 mmol) and triethylamine (10.3 mL, 73.9 mmol) in DMSO (110 mL) at 80° C. for 18 h. Pour the reaction mixture into water, rinsing with EtOAc. Extract with EtOAc. Wash the organic layer with water (2×) and brine, and dry over Na₂SO₄, and concentrate under reduced pressure. Purify the resulting residue by flash silica gel chromatography (gradient of 20% to 80% EtOAc in hexanes) to provide the title compound (4.13 g, 46%). ES/MS m/z (³⁵Cl) 363.0 (M+1).

PREPARATION 16

(S)-tert-Butyl 4-(4-(4-cyanophenyl)phthalazin-1-yl)-3-methylpiperazine-1-carboxylate

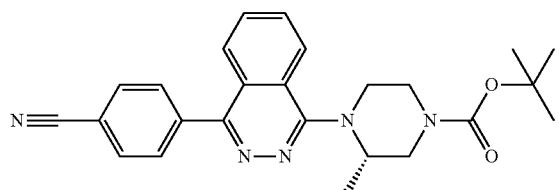

Heat a mixture of (S)-tert-butyl 4-(4-chlorophthalazin-1-yl)-3-methylpiperazine-1-carboxylate (4.0 g, 11.0 mmol), 4-cyanophenylboronic acid (2.43 g, 16.5 mmol), cesium carbonate (14.4 g, 44.1 mmol), and (SP-4-1)-bis[bis(1,1-dimethylethyl)(4-methoxyphenyl)phosphine-κP]dichloro-palladium (*J. Org. Chem.* 2007, 72, 5104-5112) (75.4 mg, 0.11 mmol) in 1,4-dioxane (80 mL) and water (20 mL) at 90° C. overnight. Partition the reaction mixture between water and CH₂Cl₂. Extract the aqueous layer with CH₂Cl₂. Dry the combined organic layer over Na₂SO₄ and concentrate under reduced pressure. Purify the resulting residue by flash silica gel chromatography (gradient of 0 to 20% EtOAc in CH₂Cl₂) to provide the title compound as a light orange foam (4.46 g, 94%). ES/MS m/z 430.2 (M+1).

Prepare the piperazinylphthalazines in the table below by essentially following the procedure described in Preparation 16, using the appropriate 4-chlorophthalazine and boronic acid. Degas Preparations 19-20 prior to adding bis(di-tert-butyl(4-dimethylaminophenyl)phosphine)dichloropalladium(II) as the catalyst, and heat the resulting mixtures at 90° C. for 72 h.

| Prep. No. | Chemical name | Structure | LC-ES/MS m/z |
|---|---|---|---|
| 17 | (S)-tert-Butyl 3-methyl-4-(4-phenylphthalazin-1-yl)piperazine-1-carboxylate | 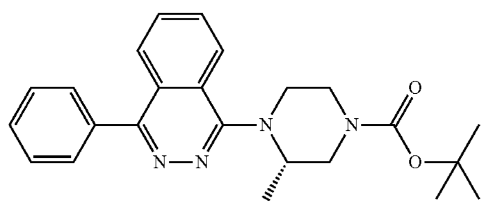 [SMILES: C[C@H]1CN(C(=O)OC(C)(C)C)CCN1c1nnc(-c2ccccc2)c2ccccc12] | 405.2 (M + 1) |
| 18 | (S)-tert-Butyl 4-(4-(4-cyanophenyl)phthalazin-1-yl)-2-methylpiperazine-1-carboxylate | 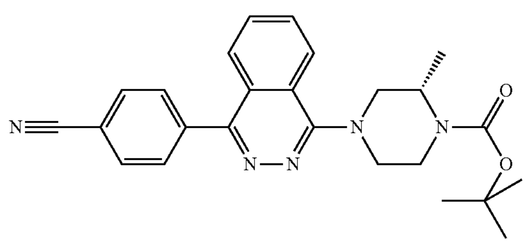 [SMILES: C[C@H]1CN(c2nnc(-c3ccc(C#N)cc3)c3ccccc23)CCN1C(=O)OC(C)(C)C] | 430.2 (M + 1) |
| 19 | (S)-tert-Butyl 2-methyl-4-(4-phenylphthalazin-1-yl)piperazine-1-carboxylate | 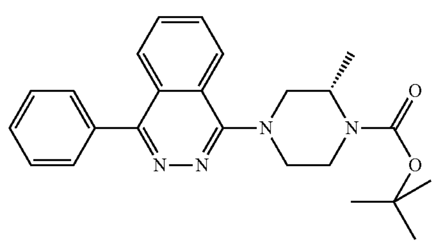 [SMILES: C[C@H]1CN(c2nnc(-c3ccccc3)c3ccccc23)CCN1C(=O)OC(C)(C)C] | 405.2 (M + 1) |
| 20 | (S)-tert-Butyl 2-methyl-4-(4-(4-(trifluoromethyl)phenyl)phthalazin-1-yl)piperazine-1-carboxylate | 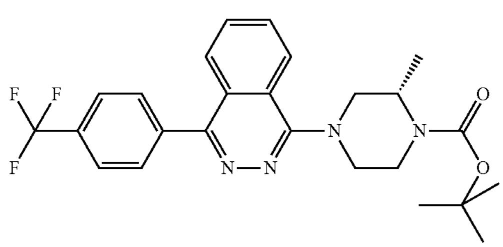 [SMILES: C[C@H]1CN(c2nnc(-c3ccc(C(F)(F)F)cc3)c3ccccc23)CCN1C(=O)OC(C)(C)C] | 473.2 (M + 1) |

PREPARATION 21

(S)-tert-Butyl 4-(4-(4-methoxyphenyl)phthalazin-1-yl)-2-methylpiperazine-1-carboxylate

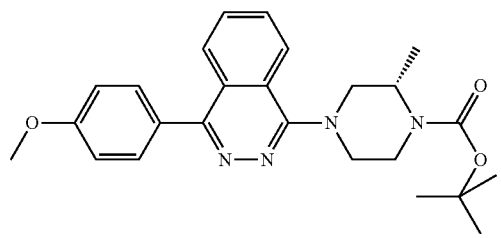 [SMILES: COc1ccc(-c2nnc(N3CCN(C(=O)OC(C)(C)C)[C@@H](C)C3)c3ccccc23)cc1]

Treat a degassed mixture of (S)-tert-butyl 4-(4-chlorophthalazin-1-yl)-2-methylpiperazine-1-carboxylate (0.81 g, 2.23 mmol), 4-methoxybenzeneboronic acid (1.07 g, 7.05 mmol) and cesium fluoride (1.05 g, 6.94 mmol) in 1,4-dioxane (30 mL) with (1,1'-bis(diphenylphosphino)ferrocene)palladium(II) chloride (0.27 g, 0.33 mmol). Heat the resulting mixture at 95° C. overnight. Partition the reaction mixture between water and EtOAc. Extract the aqueous layer with EtOAc. Wash the organic portion with water and brine, dry over $Na_2SO_4$, and concentrate under reduced pressure. Purify the resulting residue by flash silica gel chromatography (gradient of 15 to 70% EtOAc in hexanes) to provide the title compound (0.94 g, 96%). ES/MS m/z 435.2 (M+1).

PREPARATION 22

(S)-1-(4-Fluorophenyl)-4-(3-methylpiperazin-1-yl)phthalazine

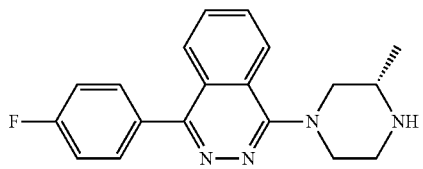 [SMILES: C[C@H]1CN(c2nnc(-c3ccc(F)cc3)c3ccccc23)CCN1]

Treat a solution of (S)-tert-butyl 4-(4-(4-fluorophenyl)phthalazin-1-yl)-2-methylpiperazine-1-carboxylate (7.05 g, 16.2 mmol) in 1,4-dioxane (50 mL) with 4 M HCl in 1,4-dioxane (25 mL). Add MeOH to dissolve the resultant precipitate and stir for 2 h at ambient temperature. Concentrate the reaction mixture under reduced pressure. Dissolve residue in MeOH and pour onto a 50 g Varian® SCX column. Rinse with MeOH and $CH_2Cl_2$, then elute the product with 1:1 $CH_2Cl_2$: 2 M ammonia in MeOH. Concentrate the eluent under reduced pressure to provide the title compound as a pale yellow foam (4.83 g, 93%). ES/MS m/z 323.2 (M+1).

Alternate Procedure for Preparation 22:

Cool methanol (2.82 L) to 0° C. via a 1:1 acetone/water bath with dry ice, and add acetyl chloride (142 mL, 2.0 mol) dropwise over a period of 30 min, maintaining the temperature below 15° C. during the addition. Stir the mixture for 15 min. Add (S)-tert-butyl 4-(4-(4-fluorophenyl)phthalazin-1-yl)-2-methylpiperazine-1-carboxylate (282 g, 667 mmol) in one portion. Stir the mixture for 12 h at 25° C. Concentrate, and dissolve the residue in water (3.0 L). Add solid $NaHCO_3$ until the pH is 7. Extract the product with $CH_2Cl_2$ (2×2.0 L), combine the organic layers, and concentrate to give the title compound as a brown crushable foam in quantitative yield (236 g, >100%). ES/MS m/z 323.0 (M+1).

Prepare the piperazinylphthalazines in the table below by essentially following the procedure described in Preparation 22, using the appropriate boc-protected piperazinylphthalazine with reaction times from 2 h to overnight. For Preparations 30-34 use MeOH as solvent.

| Prep. No. | Chemical name | Structure | LC-ES/MS m/z |
|---|---|---|---|
| 23 | (S)-1-(4-Fluorophenyl)-4-(2-methylpiperazin-1-yl)phthalazine | 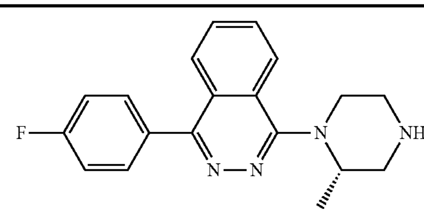 | 323.2 (M + 1) |
| 24 | (R)-1-(4-Fluorophenyl)-4-(3-methylpiperazin-1-yl)phthalazine | 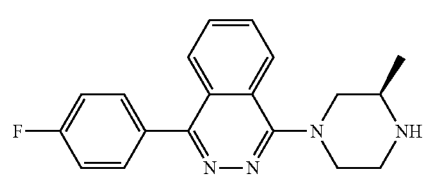 [SMILES: C[C@@H]1CN(c2nnc(-c3ccc(F)cc3)c3ccccc23)CCN1] | 323.2 (M + 1) |

-continued

| Prep. No. | Chemical name | Structure | LC-ES/MS m/z |
|---|---|---|---|
| 25 | (R)-1-(4-Fluorophenyl)-4-(2-methylpiperazin-1-yl)phthalazine | 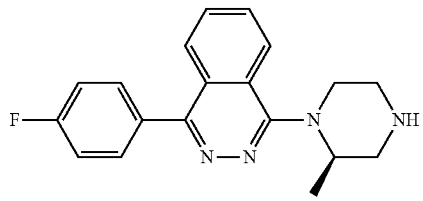 [SMILES: C[C@@H]1CNCCN1c1nnc(-c2ccc(F)cc2)c2ccccc12] | 323.2 (M + 1) |
| 26 | (±)-1-(4-Fluorophenyl)-4-(3-methylpiperazin-1-yl)phthalazine | 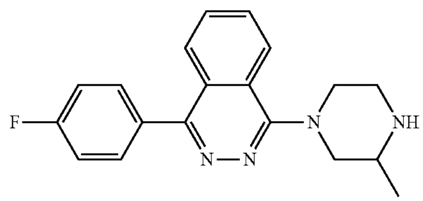 [SMILES: CC1CN(c2nnc(-c3ccc(F)cc3)c3ccccc23)CCN1] | 323.0 (M + 1) |
| 27 | (±)-1-(4-Fluorophenyl)-4-(2-methylpiperazin-1-yl)phthalazine | 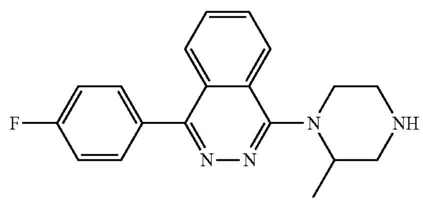 [SMILES: CC1CNCCN1c1nnc(-c2ccc(F)cc2)c2ccccc12] | 323.0 (M + 1) |
| 28 | (S)-1-(2-Methylpiperazin-1-yl)-4-phenylphthalazine | 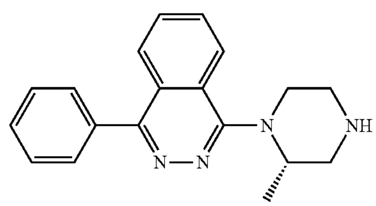 [SMILES: C[C@H]1CNCCN1c1nnc(-c2ccccc2)c2ccccc12] | 305.2 (M + 1) |
| 29 | (S)-4-(4-(2-Methylpiperazin-1-yl)phthalazin-1-yl)benzonitrile | 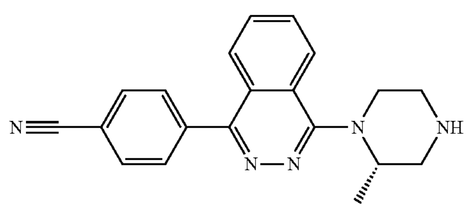 [SMILES: C[C@H]1CNCCN1c1nnc(-c2ccc(C#N)cc2)c2ccccc12] | 330.2 (M + 1) |
| 30 | (S)-1-(3-Ethylpiperazin-1-yl)-4-(4-fluorophenyl)phthalazine | 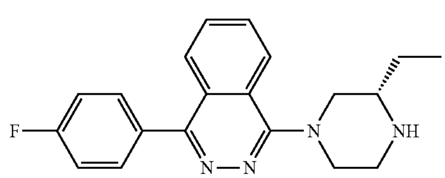 [SMILES: CC[C@H]1CN(c2nnc(-c3ccc(F)cc3)c3ccccc23)CCN1] | 337.2 (M + 1) |
| 31 | (S)-1-(3-Methylpiperazin-1-yl)-4-phenylphthalazine | 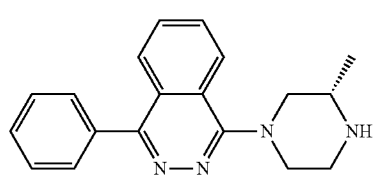 [SMILES: C[C@H]1CN(c2nnc(-c3ccccc3)c3ccccc23)CCN1] | 305.2 (M + 1) |

| Prep. No. | Chemical name | Structure | LC-ES/MS m/z |
|---|---|---|---|
| 32 | (S)-1-(3-Methylpiperazin-1-yl)-4-(4-(trifluoromethyl)phenyl)phthalazine | 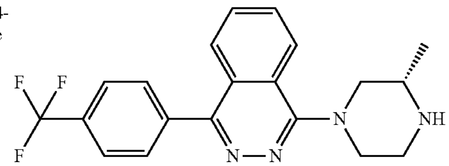 | 373.2 (M + 1) |
| 33 | (S)-4-(4-(3-Methylpiperazin-1-yl)phthalazin-1-yl)benzonitrile | 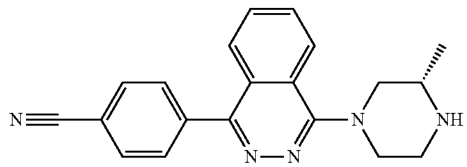 [SMILES: C[C@H]1CN(c2nnc(-c3ccc(C#N)cc3)c3ccccc23)CCN1] | 330.2 (M + 1) |
| 34 | (S)-1-(4-Methoxyphenyl)-4-(3-methylpiperazin-1-yl)phthalazine | 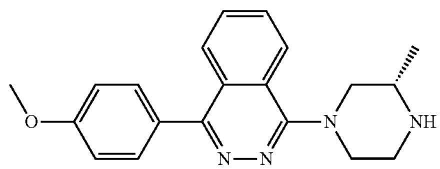 | 335.2 (M + 1) |

PREPARATION 35

3-Fluoro-4-isocyanatobenzonitrile

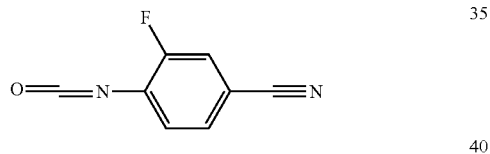

Cool a solution of triphosgene (1.09 g, 3.67 mmol) in toluene (20 mL) in an ice-water bath. Treat with a solution of a 4-amino-3-fluorobenzonitrile (1.36 g, 10.0 mmol) and triethylamine (2.8 mL, 20.0 mmol) in toluene (30 mL) dropwise. Heat the resulting mixture at 70° C. for 5 h. Cool the reaction mixture to ambient temperature and filter off the solid. Concentrate the filtrate under reduced pressure to give a white solid (1.44 g, 84%) which is used without further purification. GC/MS m/z 162 (M$^+$).

Prepare the known isocyanate in the table below from the appropriate aniline, by essentially following the procedure described in Preparation 35.

| Prep. No. | Chemical name | Structure | GC/MS m/z |
|---|---|---|---|
| 36 | 2-Fluoro-1-isocyanato-4-(trifluoromethyl)benzene | 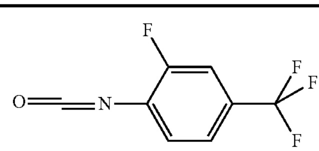 | 205 (M$^+$) |

EXAMPLE 1

(S)—N-(4-Fluorophenyl)-4-(4-(4-fluorophenyl)phthalazin-1-yl)-2-methylpiperazine-1-carboxamide hydrochloride

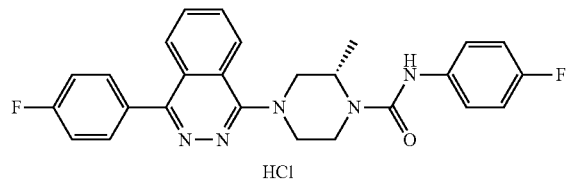 [SMILES: C[C@H]1CN(c2nnc(-c3ccc(F)cc3)c3ccccc23)CCN1C(=O)Nc1ccc(F)cc1 ; Cl]

Treat a solution of (S)-1-(4-fluorophenyl)-4-(3-methylpiperazin-1-yl)phthalazine (1.0 g, 3.1 mmol) in $CH_2Cl_2$ (31 mL) with 1-fluoro-4-isocyanatobenzene (0.42 mL, 3.72 mmol). Stir for 3 d at ambient temperature. Concentrate the reaction mixture under reduced pressure. Triturate the residue with $Et_2O$ and filter. Rinse the solid with pentane and then dry in a vacuum oven at 45° C. Dissolve the solid in a mixture of $CH_2Cl_2$ and MeOH and treat with 3 eq of 1 M HCl in $Et_2O$. Agitate the resulting mixture, concentrate under reduced pressure, and dry in a vacuum oven at 45° C. to yield the title hydrochloride salt as a yellow foam (1.5 g, 98%). ES/MS m/z 460.0 (M+1).

Alternate Procedure for Example 1:

Add 1-fluoro-4-isocyanatobenzene (105 mL, 930 mmol) dropwise over 1 h to a solution of (S)-1-(4-fluorophenyl)-4-(3-methylpiperazin-1-yl)phthalazine (300 g, 930 mmol) in $CH_2Cl_2$ (4.5 L) at 25° C. Stir the mixture for 25 min, and concentrate to a foam. Slurry the foam in MTBE (3.0 L), and wash the wet cake with MTBE (500 mL). Concentrate the mother liquor to an oil. Slurry the oil in ethyl acetate (2.0 L) to give a solid and filter. Combine the filtered solids, and dry to obtain the title compound as a tan solid (344 g, 80%). Slurry the solid (327 g, 711 mmol) in isopropanol (3.27 L) at 42° C. and treat with 4 M HCl in 1,4-dioxane (177 mL, 711 mmol). Heat the resulting mixture to 60° C. for 30 min. Cool to 25° C. slowly over 2 h. Filter and wash the wet cake with isopropanol (200 mL) and heptane (200 mL). Dry the cake in a vacuum oven (12 torr, 35° C., 2 h) to obtain the title compound as a pale yellow solid (308 g, 87%). ES/MS m/z 460.0 (M+1).

EXAMPLE 2

(S)—N-(4-Fluorophenyl)-4-(4-(4-fluorophenyl)phthalazin-1-yl)-3-methylpiperazine-1-carboxamide hydrochloride

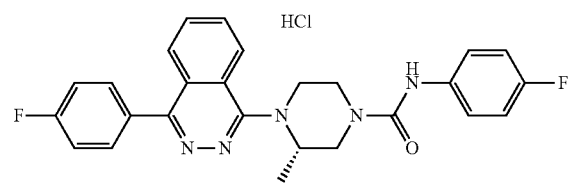 [SMILES: C[C@H]1CN(C(=O)Nc2ccc(F)cc2)CCN1c1nnc(-c2ccc(F)cc2)c2ccccc12 ; Cl]

Treat a solution of (S)-1-(4-fluorophenyl)-4-(2-methylpiperazin-1-yl)phthalazine (0.5 g, 1.55 mmol) in $CH_2Cl_2$ (15.5 mL) with 1-fluoro-4-isocyanatobenzene (0.194 mL, 1.71 mmol). Stir overnight at ambient temperature. Purify the reaction mixture by flash silica gel chromatography (gradient of 0 to 3% 2 M ammonia/MeOH in $CH_2Cl_2$). Dissolve the purified free base in a mixture of $CH_2Cl_2$ and MeOH and treat with 3 eq of 1 M HCl in $Et_2O$. Agitate the resulting mixture, concentrate under reduced pressure, and dry in a vacuum oven at 45° C. to yield the title hydrochloride salt as a yellow foam (0.72 g, 94%). ES/MS m/z 460.0 (M+1).

Alternate Procedure for Example 2:

Add 1-fluoro-4-isocyanatobenzene (27.9 mL, 245 mmol) dropwise over 1 h to a solution of (S)-1-(4-fluorophenyl)-4-(2-methylpiperazin-1-yl)phthalazine (72 g, 223 mmol) in $CH_2Cl_2$ (500 mL) at 25° C. Stir the mixture for 25 min and concentrate to a foam. Add acetyl chloride (16.5 mL, 231 mmol) to methanol at 0° 10 C. and stir for 5 min. Add the foam to the methanol solution and stir for 1 h. Concentrate the solution to a foam. Slurry the foam in acetonitrile (200 mL) and $CH_2Cl_2$ (30 mL), filter and collect the title compound as a yellow solid (91 g, 86%). ES/MS m/z 460.0 (M+1).

Prepare the ureas in the table below by essentially following the procedures described in Example 1 or Example 2, using the appropriate piperazinylphthalazine and a slight excess of the appropriate isocyanate. Reactions times vary from 0.5 h to 3 d. Purify compounds by trituration (with $Et_2O$ or 1:1 $CH_2Cl_2$: hexanes) or by flash silica gel chromatography. For Examples 57-60 and 66-69, purify by mass-guided reverse phase chromatography (Waters XBridge C18 ODB MS HPLC column, 30×75 mm, 5 μm particle size, gradient of 20 to 70% acetonitrile in water, containing 0.01 M ammonium bicarbonate, at 85 mL/min flow rate for 8 min) For Examples 75-82, use the crude isocyanates (Preparations 35-36) in 1.5-2 fold excess. For Examples 18, 29 and 38 omit MeOH from the HCl salt formation process.

| Ex. No. | Chemical name | Structure | ES/MS m/z |
|---|---|---|---|
| 3 | (±)-N-(4-Fluorophenyl)-4-(4-(4-fluorophenyl)phthalazin-1-yl)-2-methylpiperazine-1-carboxamide hydrochloride | 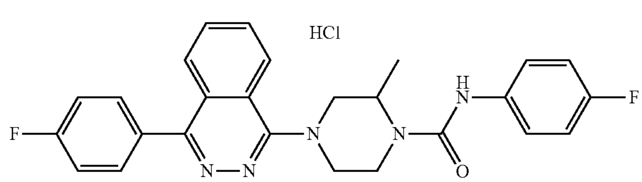 [SMILES: CC1CN(c2nnc(-c3ccc(F)cc3)c3ccccc23)CCN1C(=O)Nc1ccc(F)cc1 ; Cl] | 460.0 (M + 1) |

-continued

| Ex. No. | Chemical name | Structure | ES/MS m/z |
|---|---|---|---|
| 4 | (±)-4-(4-Fluorophenyl)phthalazin-1-yl)-2-methyl-N-(4-(trifluoromethoxy)phenyl)piperazine-1-carboxamide hydrochloride | 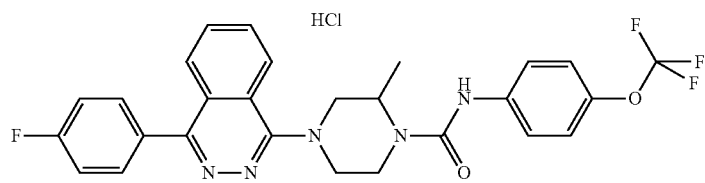 [SMILES: Cl ; CC1CN(c2nnc(-c3ccc(F)cc3)c3ccccc23)CCN1C(=O)Nc1ccc(OC(F)(F)F)cc1] | 526.0 (M + 1) |
| 5 | (±)-N-(4-Fluorophenyl)-4-(4-(4-fluorophenyl)phthalazin-1-yl)-3-methylpiperazine-1-carboxamide hydrochloride | 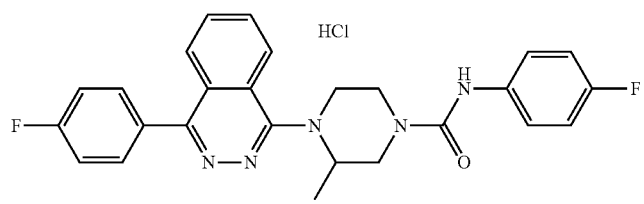 [SMILES: CC1CN(C(=O)Nc2ccc(F)cc2)CCN1c1nnc(-c2ccc(F)cc2)c2ccccc12 ; Cl] | 460.0 (M + 1) |
| 6 | (±)-4-(4-Fluorophenyl)phthalazin-1-yl)-3-methyl-N-(4-(trifluoromethoxy)phenyl)piperazine-1-carboxamide hydrochloride | 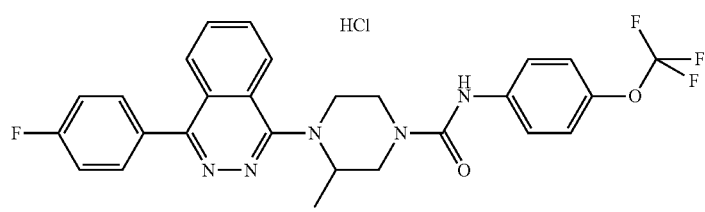 [SMILES: CC1CN(C(=O)Nc2ccc(OC(F)(F)F)cc2)CCN1c1nnc(-c2ccc(F)cc2)c2ccccc12 ; Cl] | 526.0 (M + 1) |
| 7 | (R)-N-(4-Fluorophenyl)-4-(4-(4-fluorophenyl)phthalazin-1-yl)-2-methylpiperazine-1-carboxamide hydrochloride | 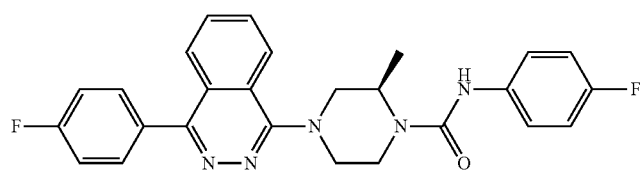 | 460.2 (M + 1) |
| 8 | (R)-4-(4-(4-Fluorophenyl)phthalazin-1-yl)-2-methyl-N-(4-(trifluoromethoxy)phenyl)piperazine-1-carboxamide hydrochloride | 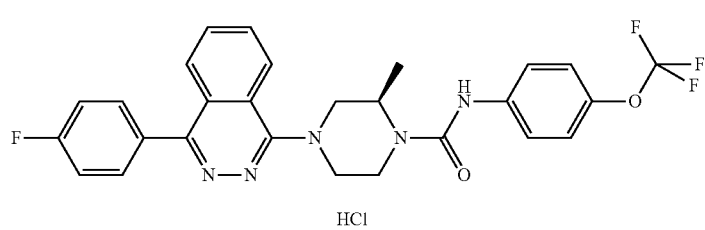 [SMILES: C[C@@H]1CN(c2nnc(-c3ccc(F)cc3)c3ccccc23)CCN1C(=O)Nc1ccc(OC(F)(F)F)cc1 ; Cl] | 526.2 (M + 1) |
| 9 | (R)-N-(4-Cyanophenyl)-4-(4-(4-fluorophenyl)phthalazin-1-yl)-2-methylpiperazine-1-carboxamide hydrochloride | 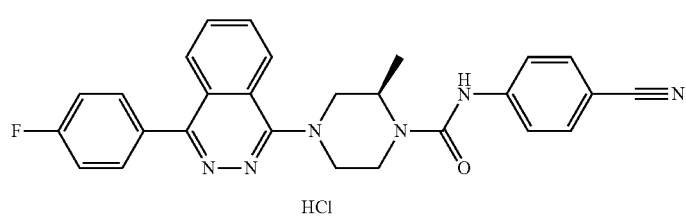 [SMILES: C[C@@H]1CN(c2nnc(-c3ccc(F)cc3)c3ccccc23)CCN1C(=O)Nc1ccc(C#N)cc1 ; Cl] | 467.2 (M + 1) |
| 10 | (R)-N-(2,4-Difluorophenyl)-4-(4-(4-fluorophenyl)phthalazin-1-yl)-2-methylpiperazine-1-carboxamide hydrochloride | 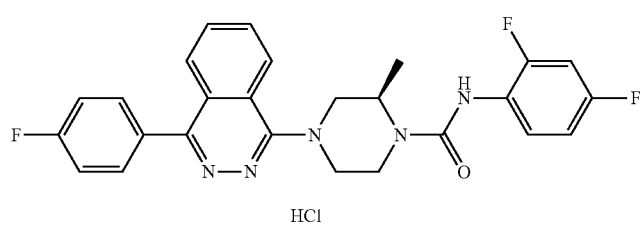 [SMILES: C[C@@H]1CN(c2nnc(-c3ccc(F)cc3)c3ccccc23)CCN1C(=O)Nc1ccc(F)cc1F ; Cl] | 478.2 (M + 1) |

-continued

| Ex. No. | Chemical name | Structure | ES/MS m/z |
|---|---|---|---|
| 11 | (R)-N-(4-Fluorophenyl)-4-(4-(4-fluorophenyl)phthalazin-1-yl)-3-methylpiperazine-1-carboxamide hydrochloride | 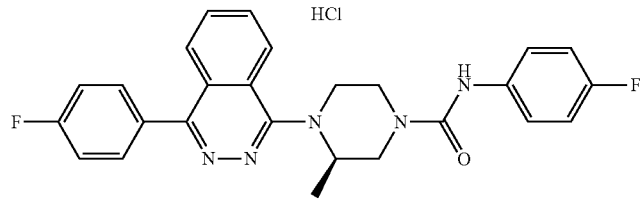 [SMILES: C[C@@H]1CN(C(=O)Nc2ccc(F)cc2)CCN1c1nnc(-c2ccc(F)cc2)c2ccccc12 ; Cl] | 460.2 (M + 1) |
| 12 | (R)-4-(4-(4-Fluorophenyl)phthalazin-1-yl)-3-methyl-N-(4-(trifluoromethoxy)phenyl)piperazine-1-carboxamide hydrochloride | 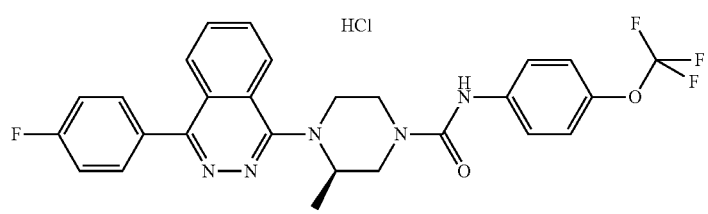 [SMILES: C[C@@H]1CN(C(=O)Nc2ccc(OC(F)(F)F)cc2)CCN1c1nnc(-c2ccc(F)cc2)c2ccccc12 ; Cl] | 526.2 (M + 1) |
| 13 | (R)-N-(4-Cyanophenyl)-4-(4-(4-fluorophenyl)phthalazin-1-yl)-3-methylpiperazine-1-carboxamide hydrochloride | 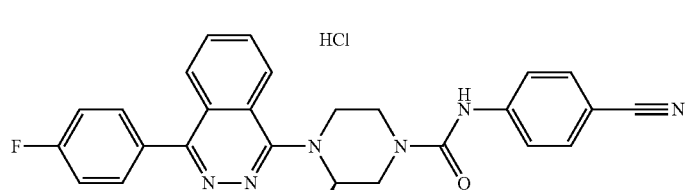 | 467.2 (M + 1) |
| 14 | (R)-N-(2,4-Difluorophenyl)-4-(4-(4-fluorophenyl)phthalazin-1-yl)-3-methylpiperazine-1-carboxamide hydrochloride | 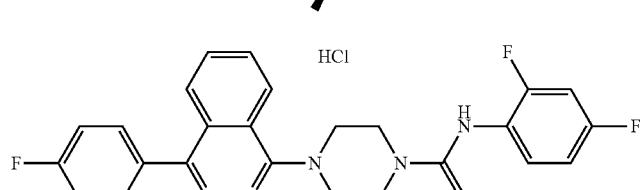 | 478.2 (M + 1) |
| 15 | (S)-4-(4-(4-Fluorophenyl)phthalazin-1-yl)-2-methyl-N-(4-(trifluoromethoxy)phenyl)piperazine-1-carboxamide hydrochloride | 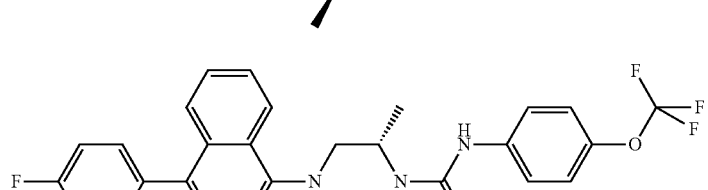 | 526.2 (M + 1) |
| 16 | (S)-N-(4-Cyanophenyl)-4-(4-(4-fluorophenyl)phthalazin-1-yl)-2-methylpiperazine-1-carboxamide hydrochloride | 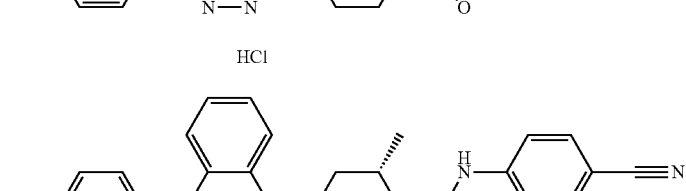 | 467.2 (M + 1) |
| 17 | (S)-N-(2,4-Difluorophenyl)-4-(4-(4-fluorophenyl)phthalazin-1-yl)-2-methylpiperazine-1-carboxamide hydrochloride | 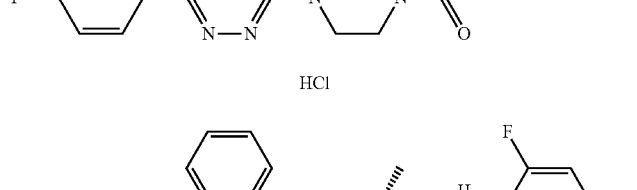 | 478.2 (M + 1) |

| Ex. No. | Chemical name | Structure | ES/MS m/z |
|---|---|---|---|
| 18 | (S)-N-(4-Fluoro-2-(trifluoromethyl)phenyl)-4-(4-(4-fluorophenyl)phthalazin-1-yl)-2-methylpiperazine-1-carboxamide hydrochloride | 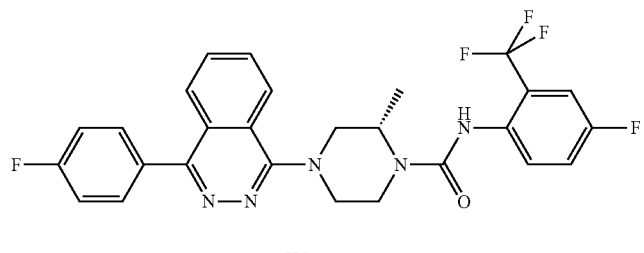 | 528.0 (M + 1) |
| 19 | (S)-N-(3-Chloro-4-fluorophenyl)-4-(4-(4-fluorophenyl)phthalazin-1-yl)-2-methylpiperazine-1-carboxamide hydrochloride | 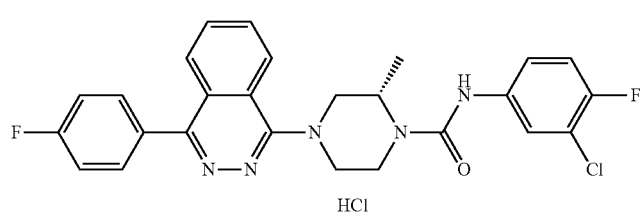 [SMILES: C[C@H]1CN(c2nnc(-c3ccc(F)cc3)c3ccccc23)CCN1C(=O)Nc1ccc(F)c(Cl)c1 ; Cl] | $^{35}$Cl 494.0 (M + 1) |
| 20 | (S)-N-(4-Chlorophenyl)-4-(4-(4-fluorophenyl)phthalazin-1-yl)-2-methylpiperazine-1-carboxamide hydrochloride | 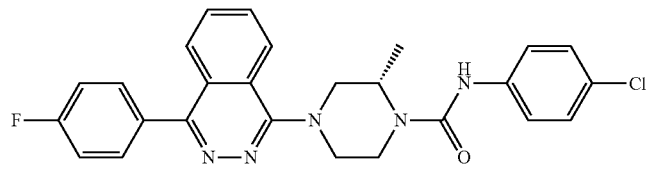 | $^{35}$Cl 476.0 (M + 1) |
| 21 | (S)-4-(4-(4-Fluorophenyl)phthalazin-1-yl)-2-methyl-N-(4-(trifluoromethyl)phenyl)piperazine-1-carboxamide hydrochloride | 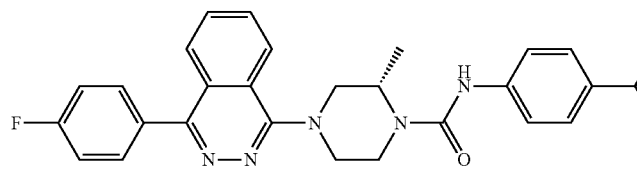 | 510.0 (M + 1) |
| 22 | (S)-N-(4-(Difluoromethoxy)phenyl)-4-(4-(4-fluorophenyl)phthalazin-1-yl)-2-methylpiperazine-1-carboxamide hydrochloride | 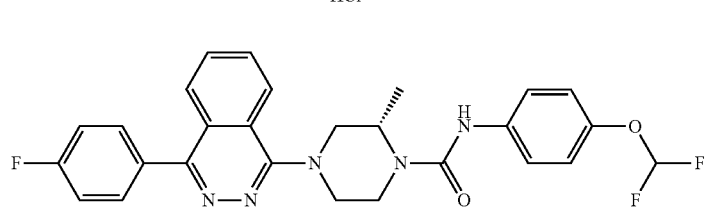 | 508.0 (M + 1) |
| 23 | (S)-4-(4-(4-Fluorophenyl)phthalazin-1-yl)-N-(4-methoxyphenyl)-2-methylpiperazine-1-carboxamide hydrochloride | 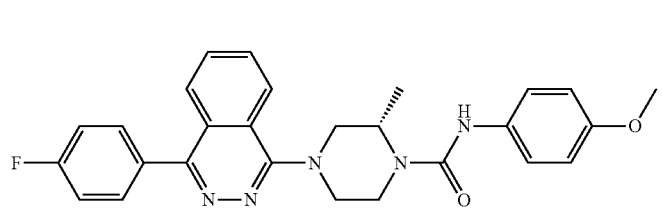 | 472.0 (M + 1) |

| Ex. No. | Chemical name | Structure | ES/MS m/z |
|---|---|---|---|
| 24 | (S)-N-(4-Cyanophenyl)-4-(4-(4-cyanophenyl)phthalazin-1-yl)-2-methylpiperazine-1-carboxamide hydrochloride | HCl | 474.2 (M + 1) |
| 25 | (S)-4-(4-(4-Cyanophenyl)phthalazin-1-yl)-N-(4-fluorophenyl)-2-methylpiperazine-1-carboxamide hydrochloride | HCl | 467.2 (M + 1) |
| 26 | (S)-4-(4-(4-Cyanophenyl)phthalazin-1-yl)-N-(2,4-difluorophenyl)-2-methylpiperazine-1-carboxamide hydrochloride | HCl | 485.0 (M + 1) |
| 27 | (S)-N-(3-Chloro-4-fluorophenyl)-4-(4-(4-cyanophenyl)phthalazin-1-yl)-2-methylpiperazine-1-carboxamide hydrochloride | HCl | $^{35}$Cl 500.8 (M + 1) |
| 28 | (S)-N-(4-Chlorophenyl)-4-(4-(4-cyanophenyl)phthalazin-1-yl)-2-methylpiperazine-1-carboxamide hydrochloride | HCl | $^{35}$Cl 483.0 (M + 1) |
| 29 | (S)-4-(4-(4-Cyanophenyl)phthalazin-1-yl)-N-(4-fluoro-2-(trifluoromethyl)phenyl)-2-methylpiperazine-1-carboxamide hydrochloride | HCl | 535.0 (M + 1) |

| Ex. No. | Chemical name | Structure | ES/MS m/z |
|---|---|---|---|
| 30 | (S)-4-(4-(4-Cyanophenyl)phthalazin-1-yl)-2-methyl-N-(4-(trifluoromethyl)phenyl)piperazine-1-carboxamide hydrochloride | 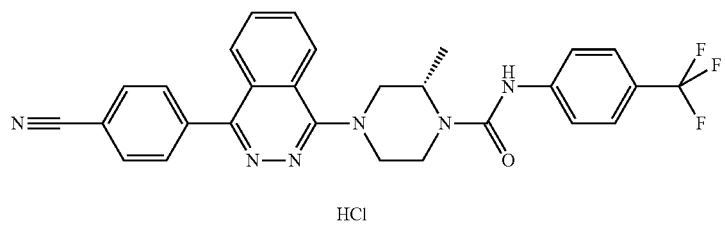 [SMILES: C[C@H]1CN(c2nnc(-c3ccc(C#N)cc3)c3ccccc23)CCN1C(=O)Nc1ccc(C(F)(F)F)cc1 ; Cl] HCl | 517.0 (M + 1) |
| 31 | (S)-4-(4-(4-Cyanophenyl)phthalazin-1-yl)-2-methyl-N-(4-(trifluoromethoxy)phenyl)piperazine-1-carboxamide hydrochloride | 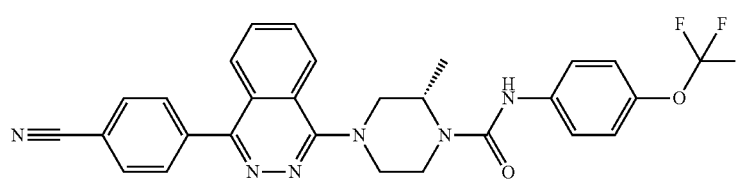 HCl | 533.0 (M + 1) |
| 32 | (S)-4-(4-(4-Cyanophenyl)phthalazin-1-yl)-N-(4-(difluoromethoxy)phenyl)-2-methylpiperazine-1-carboxamide hydrochloride | 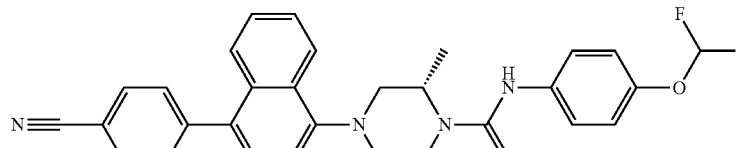 HCl | 515.0 (M + 1) |
| 33 | (S)-N-(4-Fluorophenyl)-2-methyl-4-(4-phenylphthalazin-1-yl)piperazine-1-carboxamide hydrochloride | 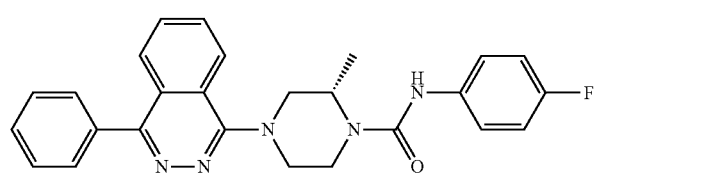 HCl | 442.2 (M + 1) |
| 34 | (S)-N-(2,4-Difluorophenyl)-2-methyl-4-(4-phenylphthalazin-1-yl)piperazine-1-carboxamide hydrochloride | 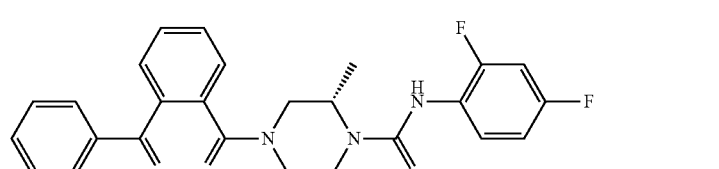 HCl | 460.2 (M + 1) |
| 35 | (S)-N-(4-Cyanophenyl)-2-methyl-4-(4-phenylphthalazin-1-yl)piperazine-1-carboxamide hydrochloride | 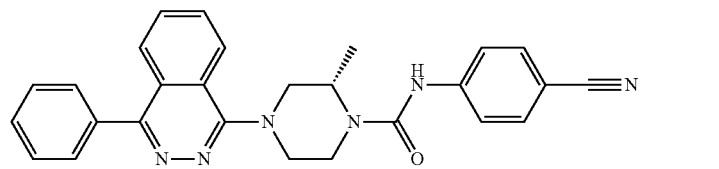 HCl | 449.2 (M + 1) |

| Ex. No. | Chemical name | Structure | ES/MS m/z |
|---|---|---|---|
| 36 | (S)-N-(3-Chloro-4-fluorophenyl)-2-methyl-4-(4-phenylphthalazin-1-yl)piperazine-1-carboxamide hydrochloride | 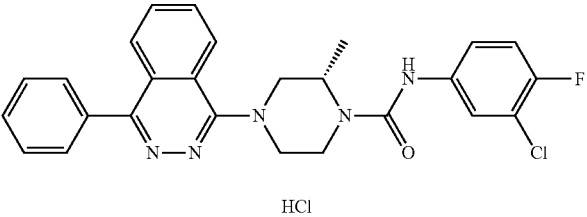 [SMILES: C[C@H]1CN(c2nnc(-c3ccccc3)c3ccccc23)CCN1C(=O)Nc1ccc(F)c(Cl)c1 ; Cl] HCl | ³⁵Cl 476.0 (M + 1) |
| 37 | (S)-N-(4-Chlorophenyl)-2-methyl-4-(4-phenylphthalazin-1-yl)piperazine-1-carboxamide hydrochloride | 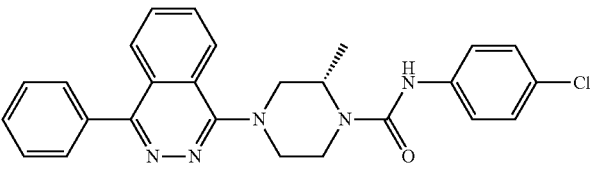 HCl | ³⁵Cl 458.0 (M + 1) |
| 38 | (S)-N-(4-Fluoro-2-(trifluoromethyl)phenyl)-2-methyl-4-(4-phenylphthalazin-1-yl)piperazine-1-carboxamide hydrochloride | 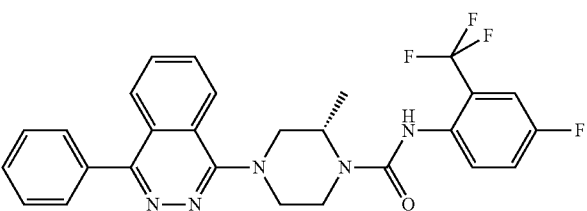 HCl | 510.0 (M + 1) |
| 39 | (S)-2-Methyl-4-(4-phenylphthalazin-1-yl)-N-(4-(trifluoromethyl)phenyl)piperazine-1-carboxamide hydrochloride | 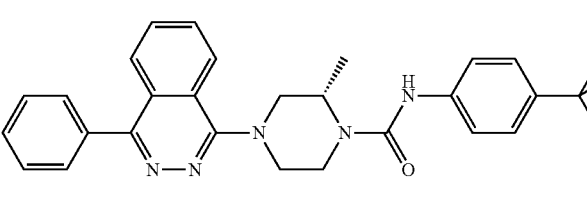 HCl | 492.0 (M + 1) |
| 40 | (S)-2-Methyl-4-(4-phenylphthalazin-1-yl)-N-(4-trifluoromethoxy)phenyl)piperazine-1-carboxamide hydrochloride | 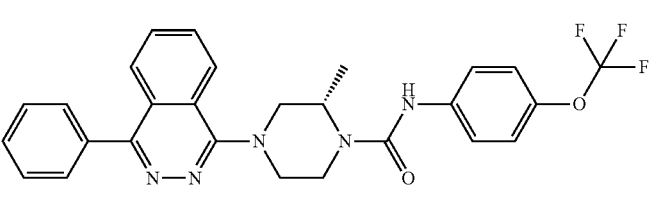 HCl | 508.0 (M + 1) |
| 41 | (S)-N-(4-(Difluoromethoxy)phenyl)-2-methyl-4-(4-phenylphthalazin-1-yl)piperazine-1-carboxamide hydrochloride | 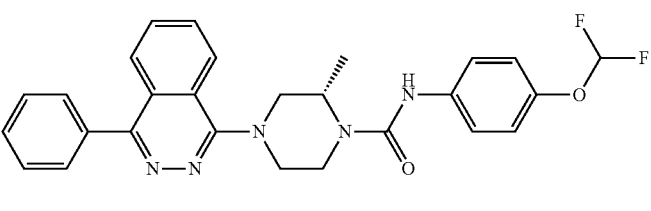 HCl | 490.0 (M + 1) |

-continued

| Ex. No. | Chemical name | Structure | ES/MS m/z |
|---|---|---|---|
| 42 | (S)-N-(4-Cyanophenyl)-4-(4-(4-ethoxyphenyl)phthalazin-1-yl)-2-methylpiperazine-1-carboxamide hydrochloride | 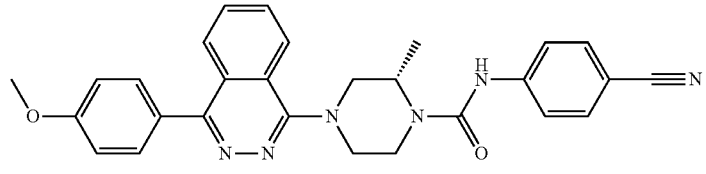 HCl | 478.8 (M + 1) |
| 43 | (S)-N-(4-Fluorophenyl)-4-(4-(4-methoxyphenyl)phthalazin-1-yl)-2-methylpiperazine-1-carboxamide hydrochloride | 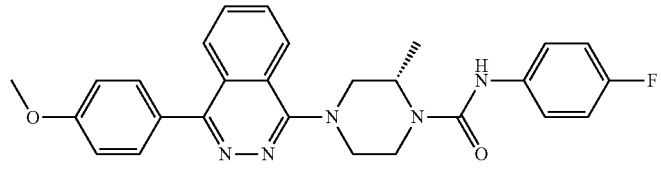 HCl | 472.2 (M + 1) |
| 44 | (S)-N-(2,4-Difluorophenyl)-4-(4-(4-methoxyphenyl)phthalazin-1-yl)-2-methylpiperazine-1-carboxamide hydrochloride | 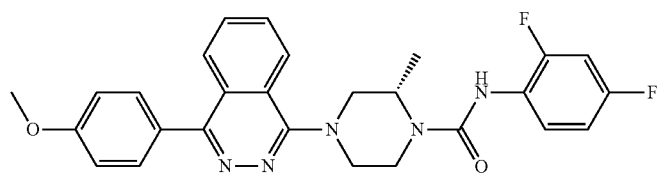 HCl | 490.2 (M + 1) |
| 45 | (S)-N-(4-Fluorophenyl)-2-methyl-4-(4-(4-(trifluoromethyl)phenyl)phthalazin-1-yl)piperazine-1-carboxamide hydrochloride | 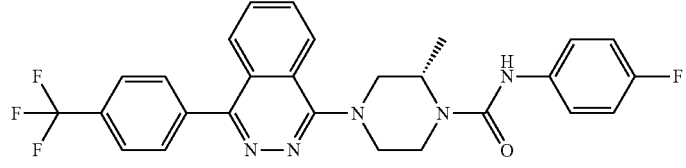 HCl | 510.2 (M + 1) |
| 46 | (S)-N-(4-Cyanophenyl)-2-methyl-4-(4-(4-(trifluoromethyl)phenyl)phthalazin-1-yl)piperazine-1-carboxamide hydrochloride | 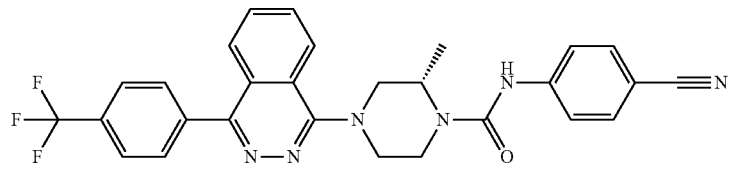 HCl | 517.2 (M + 1) |
| 47 | (S)-N-(2,4-Difluorophenyl)-2-methyl-4-(4-(4-(trifluoromethyl)phenyl)phthalazin-1-yl)piperazine-1-carboxamide hydrochloride | 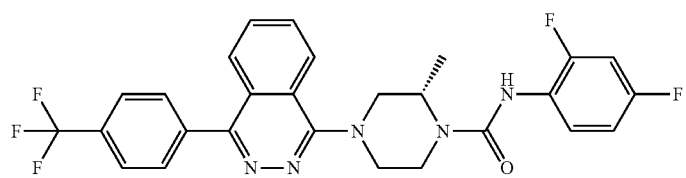 HCl | 528.0 (M + 1) |
| 48 | (S)-4-(4-(4-Fluorophenyl)phthalazin-1-yl)-3-methyl-N-(4-(trifluoromethoxy)phenyl)piperazine-1-carboxamide hydrochloride | HCl 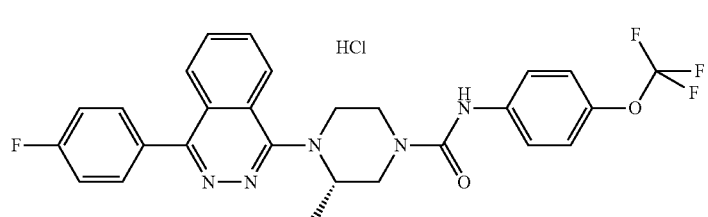 | 526.2 (M + 1) |

| Ex. No. | Chemical name | Structure | ES/MS m/z |
|---|---|---|---|
| 49 | (S)-N-(4-Cyanophenyl)-4-(4-(4-fluorophenyl)phthalazin-1-yl)-3-methylpiperazine-1-carboxamide hydrochloride | 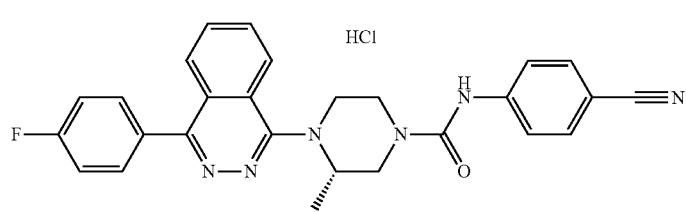 [SMILES: C[C@H]1CN(C(=O)Nc2ccc(C#N)cc2)CCN1c1nnc(-c2ccc(F)cc2)c2ccccc12 ; Cl] | 467.2 (M + 1) |
| 50 | (S)-N-(2,4-Difluorophenyl)-4-(4-(4-fluorophenyl)phthalazin-1-yl)-3-methylpiperazine-1-carboxamide hydrochloride | 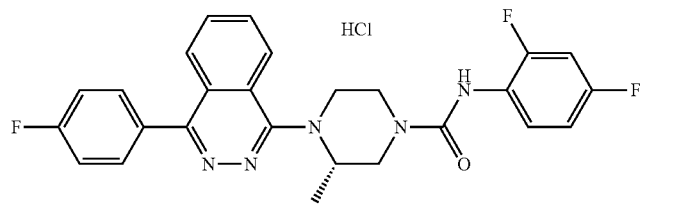 [SMILES: C[C@H]1CN(C(=O)Nc2ccc(F)cc2F)CCN1c1nnc(-c2ccc(F)cc2)c2ccccc12 ; Cl] | 478.2 (M + 1) |
| 51 | (S)-N-(4-Fluoro-2-(trifluoromethyl)phenyl)-4-(4-(4-fluorophenyl)phthalazin-1-yl)-3-methylpiperazine-1-carboxamide hydrochloride | 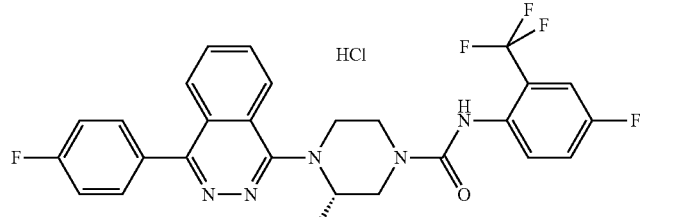 | 528.0 (M + 1) |
| 52 | (S)-4-(4-(4-Fluorophenyl)phthalazin-1-yl)-N-(4-methoxyphenyl)-3-methylpiperazine-1-carboxamide hydrochloride | 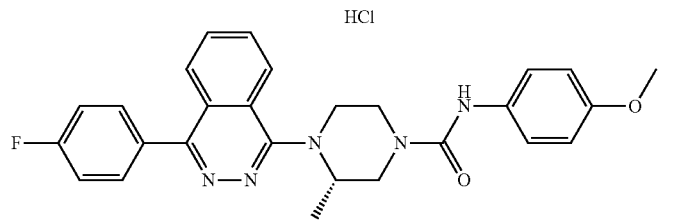 [SMILES: Cl ; COc1ccc(NC(=O)N2CCN(c3nnc(-c4ccc(F)cc4)c4ccccc34)[C@@H](C)C2)cc1] | 472.0 (M + 1) |
| 53 | (S)-N-(3-Chloro-4-fluorophenyl)-4-(4-(4-fluorophenyl)phthalazin-1-yl)-3-methylpiperazine-1-carboxamide hydrochloride | 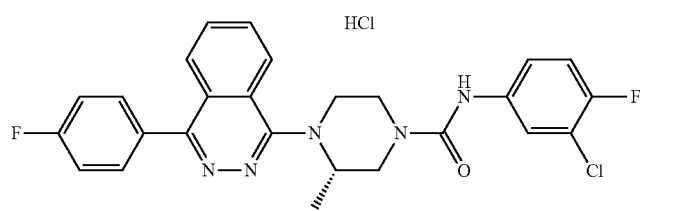 [SMILES: C[C@H]1CN(C(=O)Nc2ccc(F)c(Cl)c2)CCN1c1nnc(-c2ccc(F)cc2)c2ccccc12 ; Cl] | $^{35}$Cl 494.0 (M + 1) |
| 54 | (S)-N-(4-Chlorophenyl)-4-(4-(4-fluorophenyl)phthalazin-1-yl)-3-methylpiperazine-1-carboxamide hydrochloride | 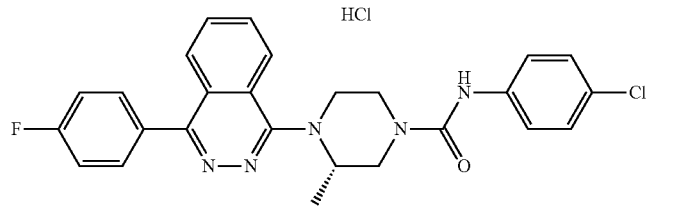 [SMILES: Cl ; C[C@H]1CN(C(=O)Nc2ccc(Cl)cc2)CCN1c1nnc(-c2ccc(F)cc2)c2ccccc12] | $^{35}$Cl 476.0 (M + 1 |
| 55 | (S)-4-(4-(4-Fluorophenyl)phthalazin-1-yl)-3-methyl-N-(4-(trifluoromethyl)phenyl) piperazine-1-carboxamide hydrochloride | 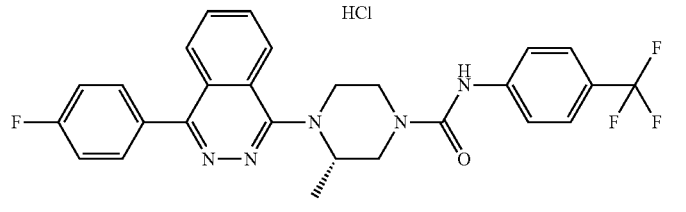 [SMILES: C[C@H]1CN(C(=O)Nc2ccc(C(F)(F)F)cc2)CCN1c1nnc(-c2ccc(F)cc2)c2ccccc12 ; Cl] | 510.0 (M + 1) |

| Ex. No. | Chemical name | Structure | ES/MS m/z |
|---|---|---|---|
| 56 | (S)-N-(4-(Difluoromethoxy)phenyl)-4-(4-(4-fluorophenyl)phthalazin-1-yl)-3-methylpiperazine-1-carboxamide hydrochloride | 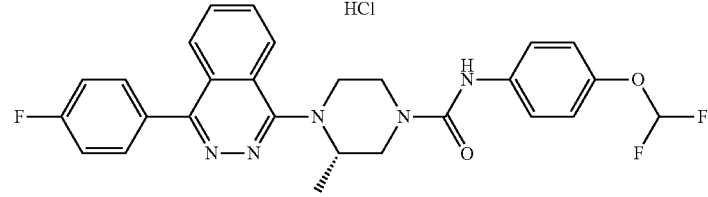 [SMILES: C[C@H]1CN(C(=O)Nc2ccc(OC(F)F)cc2)CCN1c1nnc(-c2ccc(F)cc2)c2ccccc12 ; Cl] | 508.0 (M + 1) |
| 57 | (S)-4-(4-Cyanophenyl)phthalazin-1-yl)-N-(4-fluorophenyl)-3-methylpiperazine-1-carboxamide hydrochloride | 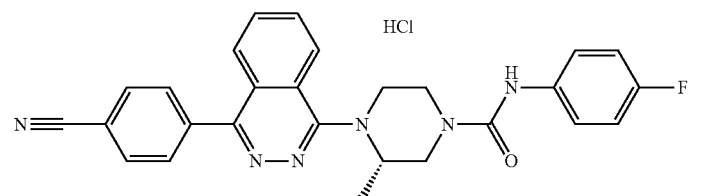 | 467.0 (M + 1) |
| 58 | (S)-N-(4-Cyanophenyl)-4-(4-(4-cyanophenyl)phthalazin-1-yl)-3-methylpiperazine-1-carboxamide hydrochloride | 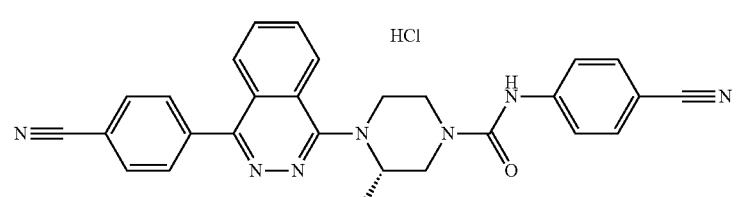 | 474.0 (M + 1) |
| 59 | (S)-4-(4-Cyanophenyl)phthalazin-1-yl)-N-(2,4-difluorophenyl)-3-methylpiperazine-1-carboxamide hydrochloride | 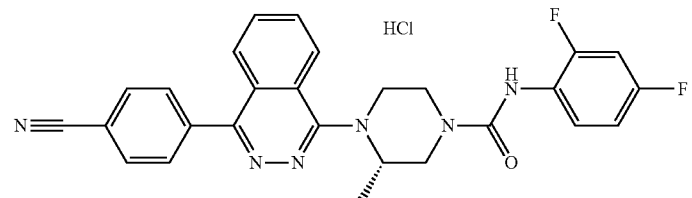 | 485.2 (M + 1) |
| 60 | (S)-4-(4-Cyanophenyl)phthalazin-1-yl)-N-(4-fluoro-2-(trifluoromethyl)phenyl)-3-methylpiperazine-1-carboxamide hydrochloride | 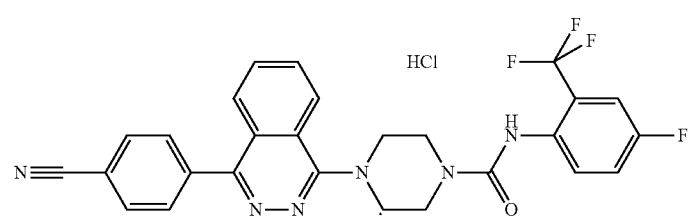 | 535.0 (M + 1) |
| 61 | (S)-N-(3-Chloro-4-fluorophenyl)-4-(4-(4-cyanophenyl)phthalazin-1-yl)-3-methylpiperazine-1-carboxamide hydrochloride | 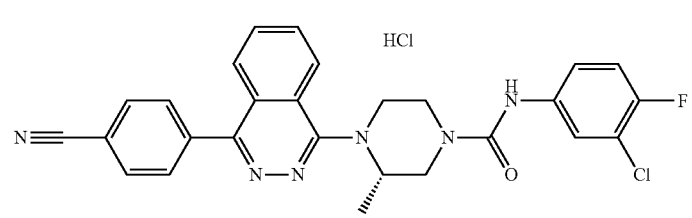 [SMILES: C[C@H]1CN(C(=O)Nc2ccc(F)c(Cl)c2)CCN1c1nnc(-c2ccc(C#N)cc2)c2ccccc12 ; Cl] | $^{35}$Cl 501.0 (M + 1) |
| 62 | (S)-N-(4-Chlorophenyl)-4-(4-(4-cyanophenyl)phthalazin-1-yl)-3-methylpiperazine-1-carboxamide hydrochloride | 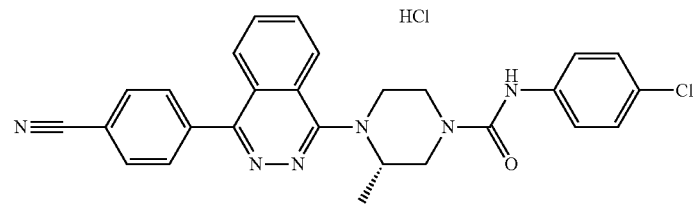 [SMILES: Cl ; C[C@H]1CN(C(=O)Nc2ccc(Cl)cc2)CCN1c1nnc(-c2ccc(C#N)cc2)c2ccccc12] | $^{35}$Cl 483.0 (M + 1) |

-continued

| Ex. No. | Chemical name | Structure | ES/MS m/z |
|---|---|---|---|
| 63 | (S)-4-(4-Cyanophenyl)phthalazin-1-yl)-3-methyl-N-(4-(trifluoromethyl)phenyl)piperazine-1-carboxamide hydrochloride | 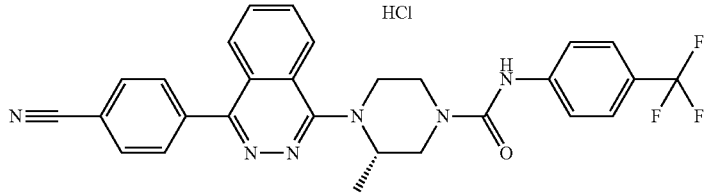 [SMILES: C[C@H]1CN(C(=O)Nc2ccc(C(F)(F)F)cc2)CCN1c1nnc(-c2ccc(C#N)cc2)c2ccccc12 ; Cl] | 517.0 (M + 1) |
| 64 | (S)-4-(4-Cyanophenyl)phthalazin-1-yl)-3-methyl-N-(4-(trifluoromethoxy)phenyl)piperazine-1-carboxamide hydrochloride | 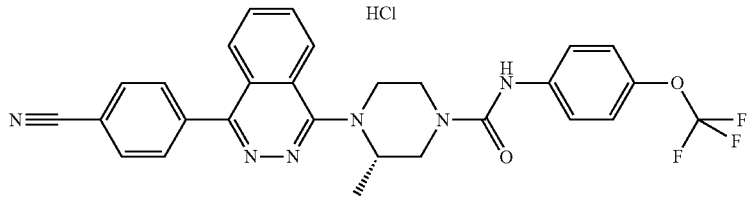 [SMILES: C[C@H]1CN(C(=O)Nc2ccc(OC(F)(F)F)cc2)CCN1c1nnc(-c2ccc(C#N)cc2)c2ccccc12 ; Cl] | 533.0 (M + 1) |
| 65 | (S)-4-(4-Cyanophenyl)phthalazin-1-yl)-N-(4-(difluoromethoxy)phenyl)-3-methylpiperazine-1-carboxamide hydrochloride | 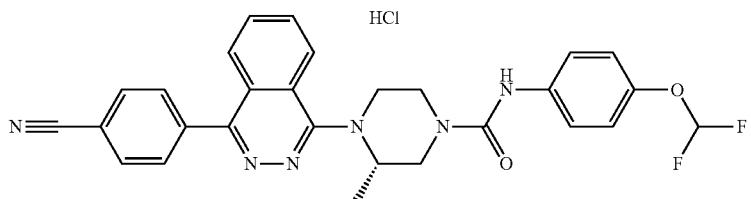 | 515.0 (M + 1) |
| 66 | (S)-N-(4-Fluorophenyl)-3-methyl-4-(4-phenylphthalazin-1-yl)piperazine-1-carboxamide hydrochloride | 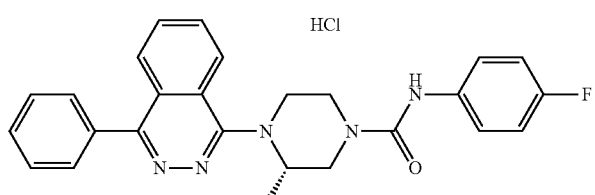 | 442.2 (M + 1) |
| 67 | (S)-N-(4-Cyanophenyl)-3-methyl-4-(4-phenylphthalazin-1-yl)piperazine-1-carboxamide hydrochloride | 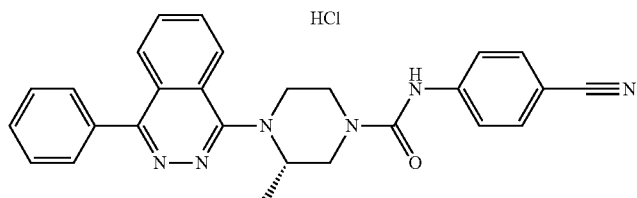 | 449.2 (M + 1) |
| 68 | (S)-N-(2,4-Difluorophenyl)-3-methyl-4-(4-phenylphthalazin-1-yl)piperazine-1-carboxamide hydrochloride | 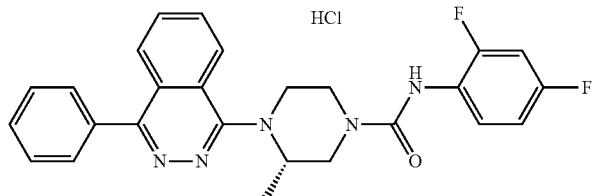 | 460.0 (M + 1) |
| 69 | (S)-N-(4-Fluoro-2-(trifluoromethyl)phenyl)-3-methyl-4-(4-phenylphthalazin-1-yl)piperazine-1-carboxamide hydrochloride | 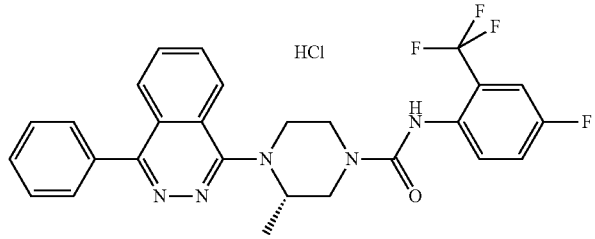 [SMILES: C[C@H]1CN(C(=O)Nc2ccc(F)cc2C(F)(F)F)CCN1c1nnc(-c2ccccc2)c2ccccc12 ; Cl] | 510.0 (M + 1) |

-continued

| Ex. No. | Chemical name | Structure | ES/MS m/z |
|---|---|---|---|
| 70 | (S)-N-(3-Chloro-4-fluorophenyl)-3-methyl-4-(4-phenylphthalazin-1-yl)piperazine-1-carboxamide hydrochloride | 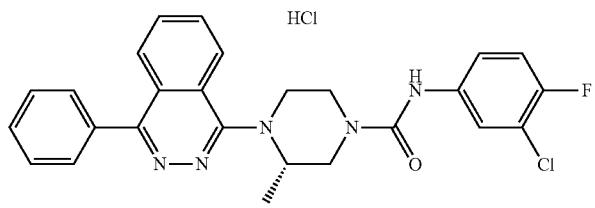 [SMILES: C[C@H]1CN(C(=O)Nc2ccc(F)c(Cl)c2)CCN1c1nnc(-c2ccccc2)c2ccccc12 ; Cl] | $^{35}$Cl 476.0 (M + 1) |
| 71 | (S)-N-(4-Chlorophenyl)-3-methyl-4-(4-phenylphthalazin-1-yl)piperazine-1-carboxamide hydrochloride | 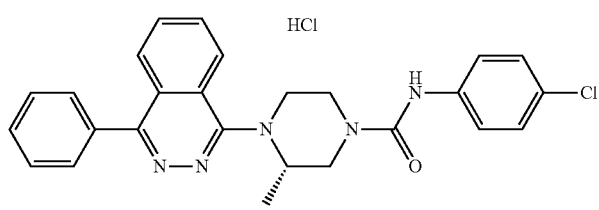 [SMILES: C[C@H]1CN(C(=O)Nc2ccc(Cl)cc2)CCN1c1nnc(-c2ccccc2)c2ccccc12 ; Cl] | $^{35}$Cl 458.0 (M + 1) |
| 72 | (S)-3-Methyl-4-(4-phenylphthalazin-1-yl)-N-(4-(trifluoromethyl)phenyl)piperazine-1-carboxamide hydrochloride | 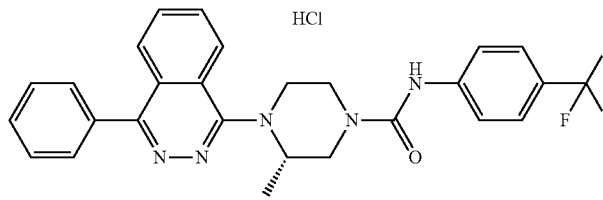 | 492.0 (M + 1) |
| 73 | (S)-3-Methyl-4-(4-phenylphthalazin-1-yl)-N-(4-(trifluoromethoxy)phenyl)piperazine-1-carboxamide hydrochloride | 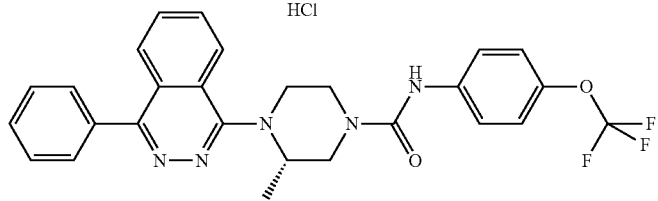 [SMILES: Cl ; C[C@H]1CN(C(=O)Nc2ccc(OC(F)(F)F)cc2)CCN1c1nnc(-c2ccccc2)c2ccccc12] | 508.0 (M + 1) |
| 74 | (S)-N-(4-(Difluoromethoxy)phenyl)-3-methyl-4-(4-phenylphthalazin-1-yl)piperazine-1-carboxamide hydrochloride | 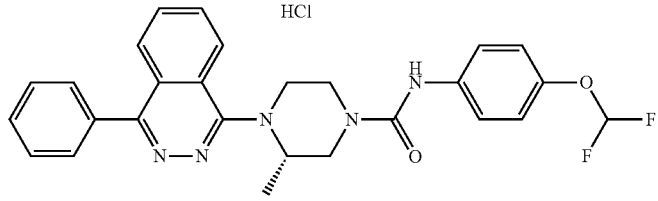 [SMILES: C[C@H]1CN(C(=O)Nc2ccc(OC(F)F)cc2)CCN1c1nnc(-c2ccccc2)c2ccccc12 ; Cl] | 490.0 (M + 1) |
| 75 | (S)-N-(4-Cyano-2-fluorophenyl)-4-(4-(4-fluorophenyl)phthalazin-1-yl)-2-methylpiperazine-1-carboxamide hydrochloride | 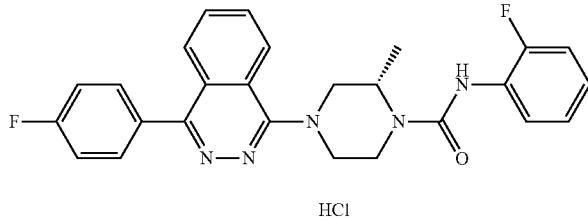 | 484.8 (M + 1) |
| 76 | (S)-N-(2-Fluoro-4-(trifluoromethyl)phenyl)-4-(4-(4-fluorophenyl)phthalazin-1-yl)-2-methylpiperazine-1-carboxamide hydrochloride | 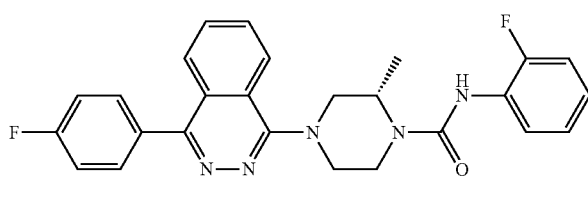 | 528.0 (M + 1) |

-continued

| Ex. No. | Chemical name | Structure | ES/MS m/z |
|---|---|---|---|
| 77 | (S)-N-(4-Cyano-2-fluorophenyl)-4-(4-(4-cyanophenyl)phthalazin-1-yl)-2-methylpiperazine-1-carboxamide hydrochloride | 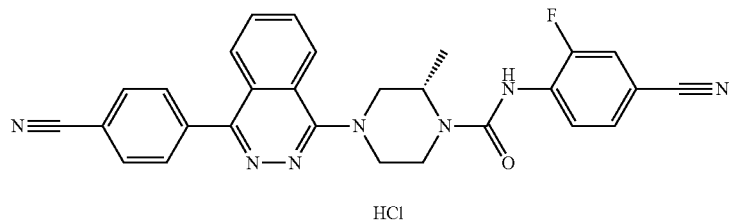 [SMILES: C[C@H]1CN(c2nnc(-c3ccc(C#N)cc3)c3ccccc23)CCN1C(=O)Nc1ccc(C#N)cc1F ; Cl] HCl | 492.0 (M + 1) |
| 78 | (S)-N-(4-Cyano-2-fluorophenyl)-2-methyl-4-(4-phenylphthalazin-1-yl)piperazine-1-carboxamide hydrochloride | 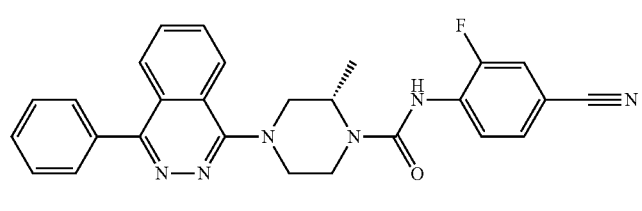 HCl | 467.0 (M + 1) |
| 79 | (S)-N-(4-Cyano-2-fluorophenyl)-4-(4-(4-fluorophenyl)phthalazin-1-yl)-3-methylpiperazine-1-carboxamide hydrochloride | 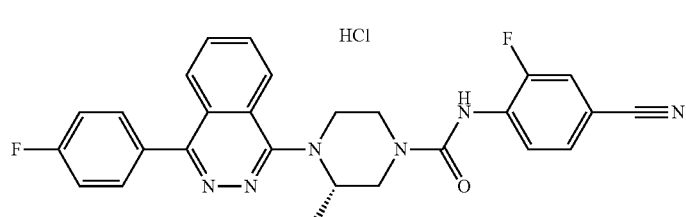 HCl | 484.8 (M + 1) |
| 80 | (S)-N-(2-Fluoro-4-(trifluoromethyl)phenyl)-4-(4-(4-fluorophenyl)phthalazin-1-yl)-3-methylpiperazine-1-carboxamide hydrochloride | 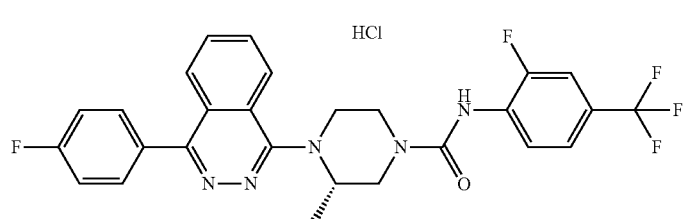 HCl | 528.0 (M + 1) |
| 81 | (S)-N-(4-Cyano-2-fluorophenyl)-4-(4-(4-cyanophenyl)phthalazin-1-yl)-3-methylpiperazine-1-carboxamide hydrochloride | 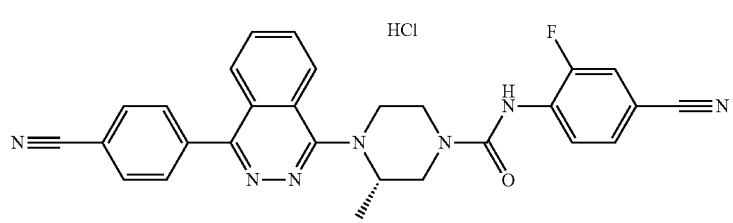 [SMILES: Cl ; C[C@H]1CN(C(=O)Nc2ccc(C#N)cc2F)CCN1c1nnc(-c2ccc(C#N)cc2)c2ccccc12] HCl | 492.0 (M + 1) |
| 82 | (S)-N-(4-Cyano-2-fluorophenyl)-3-methyl-4-(4-phenylphthalazin-1-yl)piperazine-1-carboxamide hydrochloride | 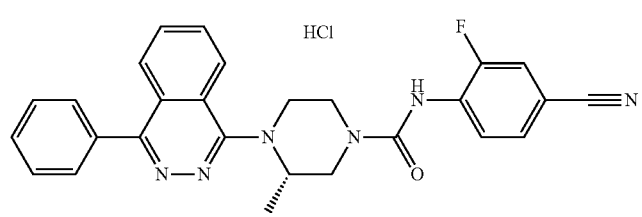 [SMILES: C[C@H]1CN(C(=O)Nc2ccc(C#N)cc2F)CCN1c1nnc(-c2ccccc2)c2ccccc12 ; Cl] HCl | 467.0 (M + 1) |
| 83 | N-(4-Cyanophenyl)-4-(4-(4-fluorophenyl)phthalazin-1-yl)-cis-2,6-dimethylpiperazine-1-carboxamide hydrochloride | 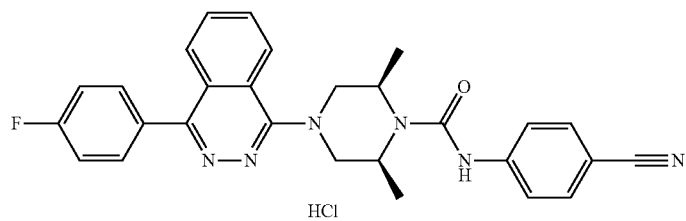 [SMILES: C[C@@H]1CN(c2nnc(-c3ccc(F)cc3)c3ccccc23)C[C@H](C)N1C(=O)Nc1ccc(C#N)cc1 ; Cl] HCl | 481.2 (M + 1) |

| Ex. No. | Chemical name | Structure | ES/MS m/z |
|---|---|---|---|
| 84 | N-(4-Fluorophenyl)-4-(4-(4-fluorophenyl)phthalazin-1-yl)-cis-2,6-dimethylpiperazine-1-carboxamide hydrochloride | 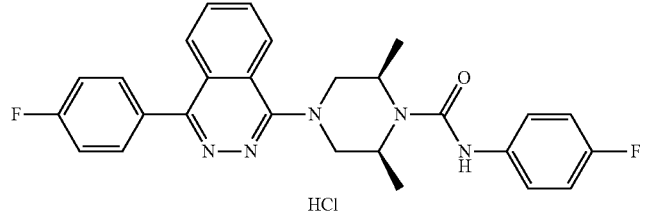 [SMILES: C[C@@H]1CN(c2nnc(-c3ccc(F)cc3)c3ccccc23)C[C@H](C)N1C(=O)Nc1ccc(F)cc1 ; Cl] | 474.2 (M + 1) |
| 85 | (S)-N-(4-Cyanophenyl)-2-ethyl-4-(4-(4-fluorophenyl)phthalazin-1-yl)piperazine-1-carboxamide hydrochloride | 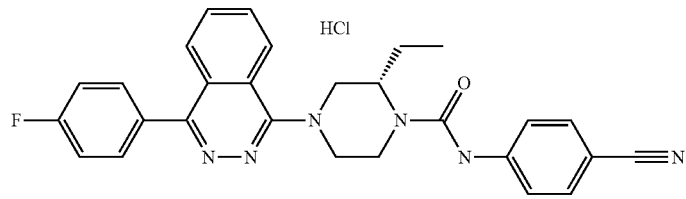 [SMILES: CC[C@H]1CN(c2nnc(-c3ccc(F)cc3)c3ccccc23)CCN1C(=O)Nc1ccc(C#N)cc1 ; Cl] | 481.2 (M + 1) |
| 86 | (S)-N-(2,4-Difluorophenyl)-2-ethyl-4-(4-(4-fluorophenyl)phthalazin-1-yl)piperazine-1-carboxamide hydrochloride | 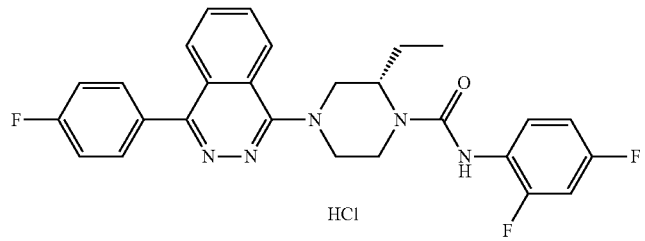 [SMILES: CC[C@H]1CN(c2nnc(-c3ccc(F)cc3)c3ccccc23)CCN1C(=O)Nc1ccc(F)cc1F ; Cl] | 492.2 (M + 1) |
| 87 | (S)-2-Ethyl-N-(4-fluoro-2-(trifluoromethyl)phenyl)-4-(4-(4-fluorophenyl)phthalazin-1-yl)piperazine-1-carboxamide hydrochloride | 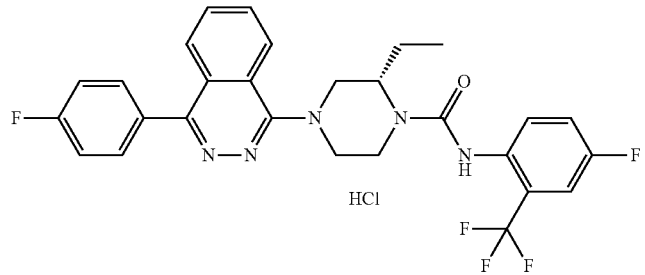 [SMILES: CC[C@H]1CN(c2nnc(-c3ccc(F)cc3)c3ccccc23)CCN1C(=O)Nc1ccc(F)cc1C(F)(F)F ; Cl] | 542.2 (M + 1) |
| 88 | (S)-2-Ethyl-N-(4-fluorophenyl)-4-(4-(4-fluorophenyl)phthalazin-1-yl)piperazine-1-carboxamide hydrochloride | 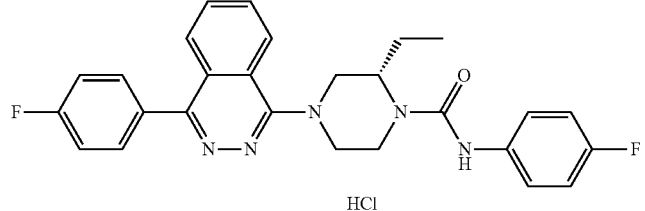 [SMILES: CC[C@H]1CN(c2nnc(-c3ccc(F)cc3)c3ccccc23)CCN1C(=O)Nc1ccc(F)cc1 ; Cl] | 474.2 (M + 1) |
| 89 | (2S,5S)-N-(4-Cyanophenyl)-4-(4-(4-fluorophenyl)phthalazin-1-yl)-2,5-dimethylpiperazine-1-carboxamide hydrochloride | 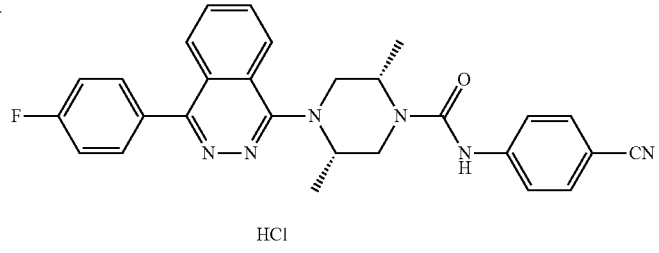 | 481.0 (M + 1) |

EXAMPLE 90

(R)—N-(4-Fluorophenyl)-4-(4-(4-fluorophenyl)phthalazin-1-yl)-2-(hydroxymethyl)piperazine-1-carboxamide hydrochloride

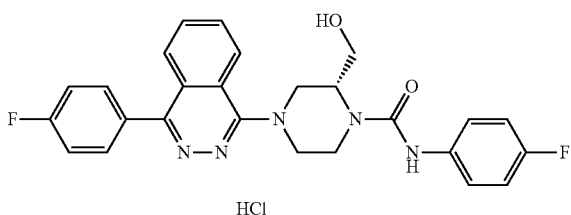 [SMILES: O=C(Nc1ccc(F)cc1)N1CCN(c2nnc(-c3ccc(F)cc3)c3ccccc23)C[C@@H]1CO ; Cl]

Treat a solution of (R)-(4-(4-(4-fluorophenyl)phthalazin-1-yl)piperazin-2-yl)-methanol (0.15 g, 0.44 mmol) in CH$_2$Cl$_2$ (3 ml) with 1-fluoro-4-isocyanatobenzene (0.04 g, 0.31 mmol). Stir the reaction at ambient temperature for 30 min and then concentrate the reaction mixture. Purify the resulting residue by flash silica gel chromatography (0-50% EtOAc in hexanes, then switch to 3% MeOH in CH$_2$Cl$_2$) to yield a solid. Dissolve the solid in MeOH (1 mL) and treat with 1 N aqueous HCl (0.13 mL, 0.13 mmol). Concentrate the solution to obtain the title compound as a solid (0.065 g, 29%). ES/MS m/z 476.0 (M+1).

Prepare the piperazinylphthalazine ureas in the table below by essentially following the procedure described in Example 90, using the appropriate piperazinylphthalazine and isocyanate.

| Ex. No. | Chemical name | Structure | ES/MS m/z |
|---|---|---|---|
| 91 | (R)-N-(4-Fluorophenyl)-4-(4-(4-fluorophenyl)phthalazin-1-yl)-2-(hydroxymethyl)piperazine-1-carboxamide hydrochloride | 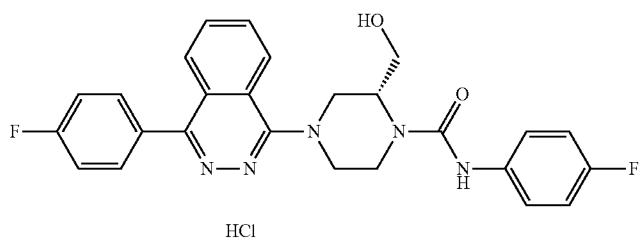 [SMILES: O=C(Nc1ccc(F)cc1)N1CCN(c2nnc(-c3ccc(F)cc3)c3ccccc23)C[C@@H]1CO ; Cl] | 476.0 (M + 1) |
| 92 | (S)-N-(4-Fluorophenyl)-4-(4-(4-fluorophenyl)phthalazin-1-yl)-2-(hydroxymethyl)piperazine-1-carboxamide hydrochloride | 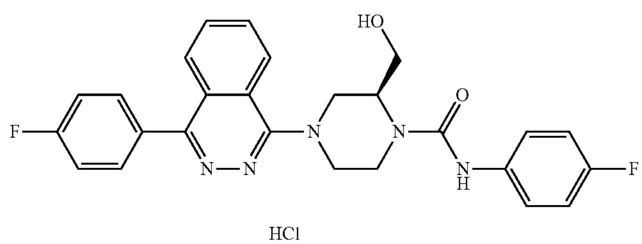 [SMILES: O=C(Nc1ccc(F)cc1)N1CCN(c2nnc(-c3ccc(F)cc3)c3ccccc23)C[C@H]1CO ; Cl] | 476.0 (M + 1) |
| 93 | (R)-N-(4-Cyanophenyl)-4-(4-(4-fluorophenyl)phthalazin-1-yl)-2-(hydroxymethyl)piperazine-1-carboxamide hydrochloride | 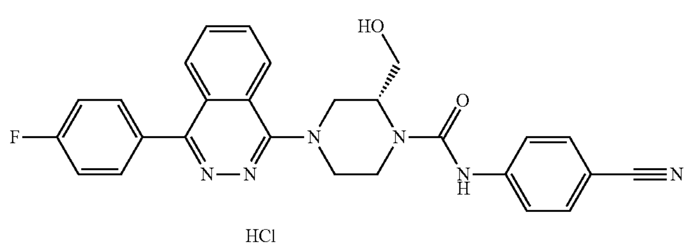 [SMILES: N#Cc1ccc(NC(=O)N2CCN(c3nnc(-c4ccc(F)cc4)c4ccccc34)C[C@@H]2CO)cc1 ; Cl] | 483.0 (M + 1) |

EXAMPLES 94 & 95

N-(4-Fluorophenyl)-4-(4-(4-fluorophenyl)phthalazin-1-yl)-trans-2,5-dimethylpiperazine-1-carboxamide hydrochloride, Isomer 1 and Isomer 2

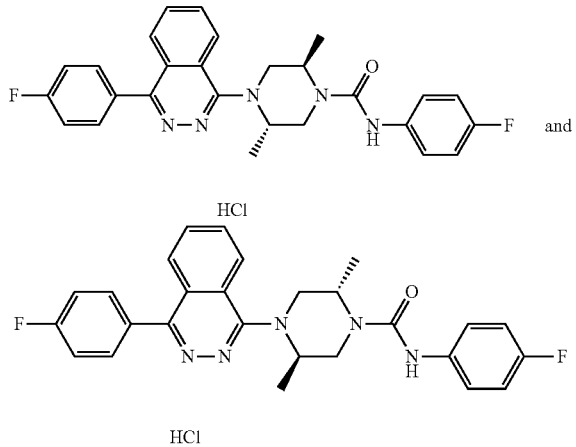

Treat a solution of 1-(trans-2,5-dimethylpiperazin-1-yl)-4-(4-fluorophenyl)phthalazine (0.3 g, 0.89 mmol) in $CH_2Cl_2$ (5 mL) with 1-fluoro-4-isocyanatobenzene (0.17 g, 1.25 mmol). Stir the reaction at ambient temperature for 1 h. Purify the reaction mixture by flash silica gel chromatography (0-50% EtOAc in hexanes). Pool and concentrate the appropriate fractions. Dissolve the mixture of N-(4-fluorophenyl)-4-(4-(4-fluorophenyl) phthalazin-1-yl)-trans-2,5-dimethylpiperazine-1-carboxamide isomers (0.3 g, 0.59 mmol) in MeOH (2 mL). Separate the mixture of trans-isomers by chiral chromatography (Chiralcel OJ-H, flow rate 30 mL/min, detection 225 nm, 6:4 MeOH: acetonitrile). Collect first eluting peak as Isomer 1 and the second eluting peak as Isomer 2. Pool and concentrate appropriate fractions. Dissolve the separated isomers in MeOH (1 mL) and treat each solution with 1 equivalent of 1 N aqueous HCl. Concentrate to give the hydrochloride salts of Isomer 1 (0.131 g, 44%) and Isomer 2 (0.129 g, 43%). Isomer 1: ES/MS m/z 474.2 (M+1), 99% ee. Isomer 2: ES/MS m/z 474.2 (M+1), 99% ee.

EXAMPLES 96 & 97

N-(4-Fluorophenyl)-4-(4-(4-fluorophenyl)phthalazin-1-yl)-cis-2,5-dimethylpiperazine-1-carboxamide hydrochloride, Isomer 1 and Isomer 2

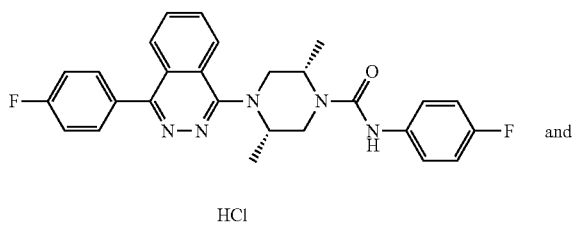

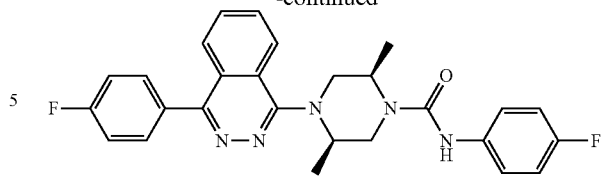

Prepare Examples 96 and 97, by essentially following the procedure as described for Examples 94 and 95, using the mixture of cis-dimethylpiperazines from Preparation 12. Separate the mixture of cis-isomers by chiral HPLC and make the HCl salts to give Isomer 1 (0.21 g, 34%) and Isomer 2 (0.20 g, 33%). Isomer 1: ES/MS m/z 474.2 (M+1), 95% ee. Isomer 2: ES/MS m/z 474.2 (M+1), 92% ee.

Biology

Hedgehog has been implicated as a survival factor for the following cancers: basal cell carcinoma; upper gastro intestinal tract cancers (esophagus, stomach, pancreas, and biliary tract); prostate cancer; breast cancer; small cell lung cancer; non-small cell lung cancer; B-cell lymphoma; multiple myeloma; gastric cancer; ovarian cancer; colorectal cancer; liver cancer; melanoma; kidney cancer; and brain cancer.

Elements of the hedgehog pathway have been asserted to be potential drug targets for the treatment of cancers. A Daoy cell line established from medulloblastoma tumor (ATCC, HTB-186), is responsive to Hh ligands. When these cells are treated with exogenously added Shh-conditioned media, Hh signaling pathway is activated and results in an increased expression of Gli1. Cyclopamine, an alkaloid isolated from the corn lily *Veratrum californicum* is a weak hedgehog antagonist and has been shown to suppress the expression of Gli1 in response to Shh stimulation. Recent observations suggest that cyclopamine inhibits the growth of cultured medulloblastoma cells and allografts. Using this Daoy cell model system, potent inhibitors of hedgehog signaling pathways can be identified. Since the compounds of the present invention are hedgehog antagonists, they are suitable for treating the aforementioned tumor types.

Determination of Biological Activity $IC_{50}$

The following assay protocol and results thereof further demonstrate the utility and efficacy of the compounds and methods of the current invention. Functional assays provide support that the compounds of the present invention exhibit the ability to inhibit Shh signaling. All ligands, solvents, and reagents employed in the following assay are readily available from commercial sources or can be readily prepared by one skilled in the art.

Biological activity is determined using a functional assay in Daoy neuronal cancer cells and measures levels of Gli1 ribonucleic acid via a bDNA (branched deoxyribonucleic acid) assay system (Panomics, Inc., Fremont, Calif.). Gli was originally discovered in a Glioblastoma cell line and encodes a zinc finger protein that is activated by Shh signaling. The maximum response is obtained by inducing Gli1 transcription in the Daoy cells with conditioned medium (human embryonic kidney, HEK-293 cells stably expressing recombinant Shh) for 24 hours and then measuring the amount of stimulated Gli1 transcript. The minimum response is the amount of Gli1 transcript inhibited with a control compound in Daoy cells that have been stimulated with conditioned media (human embryonic kidney, HEK-293 cells stably expressing recombinant Shh) for 24 hours.

Functional Assay for Measuring the Inhibition of Gli1 in Daoy cells

The bDNA assay system utilizes the technology of branched-chain DNA to allow amplification of a target ribonucleic acid (transcript). The technology employs three types of synthetic hybrid short Gil1-specific cDNA probes that determine the specificity of the target transcript [capture extenders (CEs), label extenders (LEs), and blockers (BLs)] that hybridize as a complex with the target transcripts to amplify the hybridization signal. The addition of a chemilumigenic substrate during the amplification step allows for detection using luminescence.

The Daoy cell line obtained from American Type Culture collection (ATCC) is a Shh-responsive human neuronal tumor cell line and was established in 1985 from a desmoplastic cerebellar medullablastoma tumor, a physiologically relevant tumor cell line. Endogenous levels of Gli1 transcripts levels are low in Daoy cells but can be stimulated by using conditioned media taken from cells stably over-expressing human Shh (a HEK-293 cell line stably transfected with hShh).

Daoy cells are grown to confluency in tissue culture T225-flasks in Daoy growth media containing Minimum Essential Medium (MEM) plus 10% Fetal Bovine Serum (FBS) with 0.1 nM non-essential amino acids and 1 mM sodium pyruvate. The cells are removed from the T225-flasks using trypsin ethylenediaminetetraacetic acid (EDTA), centrifuged, resuspended in media, and then counted.

The Daoy cells are then seeded at 50,000 cells per well in growth media in Costar 96 well clear tissue culture plates and allowed to incubate overnight at 37° C. under 5% carbon dioxide ($CO_2$). The cells are washed one time in phosphate buffered saline (PBS) followed by addition of 100 µL of Shh Conditioned Media (Shh-CM) to stimulate levels of Gli1 expression. Shh-CM is diluted to achieve maximum stimulation using control growth media –0.1% FBS/DMEM (Dulbeccos Modified Eagle Medium). Daoy cells treated with Shh-CM are then treated with various concentrations of hedgehog inhibitors ranging from approximately 1 µM to 0.1 nM. Test compounds are allowed to incubate for 24 hours at 37° C. under 5% $CO_2$.

The measurement of the Gli1 transcript is performed by using the Quantigene 2.0 Gli1 assay as described by the manufacturer (Panomics, Inc.). Prepare a diluted lysis mixture (DLM) buffer, which includes Proteinase K. After a 24 hour incubation with compound, the cells are washed one time with PBS and 180 µL of DLM is added to the cells. The cell plate containing the lysis buffer is sealed and placed at 55° C. for 30 to 45 minutes. The resulting cell lysates are then triturated 5 times. A working probe set containing Gli1 probes is made by diluting the probes in the DLM according to the manufacturer's directions, and then 20 µL of the working probe set is added to the bDNA assay plates along with 80 µL of the Daoy lysates. The plates are sealed and incubated overnight at 55° C. The bDNA plates are then processed according to the manufacturer's directions. The signal is quantified by reading the plates on a Perkin Elmer Envision reader detecting luminescence. The luminescent signal is directly proportional to the amount of target transcript present in the sample.

The luminescent signal data from the functional assay are used to calculate the $IC_{50}$ for the in vitro assay. The data are calculated based on the maximum control values (Daoy cells treated with Shh-CM) and the minimum control value (Daoy cells treated with Shh-CM and an inhibitory concentration of a control compound, 1 µM of N-(3-(1H-benzo[d]imidazol-2-yl)-4-chlorophenyl)-3,5-dimethoxybenzamide). A four parameter logistic curve fit is used to generate the $IC_{50}$ values using ActivityBase software programs version 5.3, equation 205 (*Assay Guidance Manual Version* 5.0, 2008, Eli Lilly and Company and NIH Chemical Genomics Center).

Following the protocol described, the compounds of the invention exemplified herein display an $IC_{50}$ of <40 nM. For example, the compound of Example 2 has an $IC_{50}$ of approximately 0.42 nM with a standard error of 0.21 (n=2) in the assay described above. These results provide evidence that the compounds of the present invention are hedgehog antagonists and, as such, are useful as anticancer agents.

CYP3A4 Inhibition Assay

Incubation samples are prepared by adding a human liver microsomal preparation to the test inhibitor (final concentrations 0.05 mg/mL protein, 10 µM inhibitor in 100 mM $NaPO_4$, pH 7.4 buffer) and mixed. Samples are pre-incubated for approximately five minutes at 37° C. Following the pre-incubation period, the reaction is initiated with the addition of a solution containing NADPH and midazolam, as the enzyme substrate, (final concentration 1 mM NADPH, 5 µM midazolam). After addition of the NADPH solution, the samples are incubated for 3 min at approximately 37° C. Following the incubation period, the reaction is quenched by the addition of 50 µL of methanol (and an internal standard for chromatography) and the samples are mixed well. After quenching the reaction, the mixture is centrifuged at approximately 4000 rpm for 15 min at approximately 5° C. and analyzed by LC/MS analysis.

Samples are analyzed using HPLC/MS with gradient elution on short conventional C18 columns, (Loading Mobile Phase—95/5 Milli-Q $H_2O$/methanol (v/v) with 1% acetic acid. Mobile Phase B—80/20 Milli-Q $H_2O$/methanol (v/v) with 1% acetic acid. Mobile Phase C—5/95 Milli-Q $H_2O$/methanol (v/v) with 1% acetic acid. Rinsing Mobile Phase—75/25 Milli-Q $H_2O$/acetonitrile (v/v).

The samples are injected into a Mass Spectral Analyzer for Selected Ion Monitoring (SIM) at a mass of 342.1 (1-OH-midazolam) and 346.1 (α-hydroxymidazolam-d4 internal standard) using Turbolon Spray under positive conditions. Data are reported as % inhibition of the formation of 1-OH-midazolam in the presence of an inhibitor concentration of 10 µM.

Following the protocol described, the following compounds of the invention exemplified herein (Examples 1-18, 26, 33-35, 44-51, 57-60, 66-69, and 85-94) display <45% inhibition. In addition, the compounds of Examples 1-5, 7-17, 33-35, 44, 46, 49-51, 57-59, 66-68, 85, and 89-94 display <10% inhibition.

We claim:
1. A compound of the following formula:

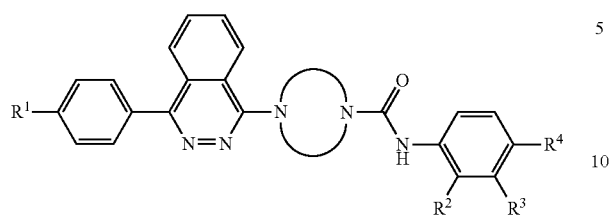

wherein,
$R^1$ is hydrogen, fluoro, cyano, trifluoromethyl or methoxy;
$R^2$ is hydrogen, fluoro or trifluoromethyl;
$R^3$ is hydrogen or chloro, provided that at least one of $R^2$ and $R^3$ is hydrogen;
$R^4$ is chloro, fluoro, cyano, trifluoromethyl, difluoromethoxy, methoxy or trifluoromethoxy;

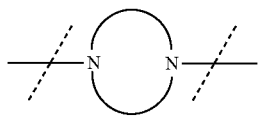

represents a substituted piperazine-1,4-diyl selected from the group consisting of

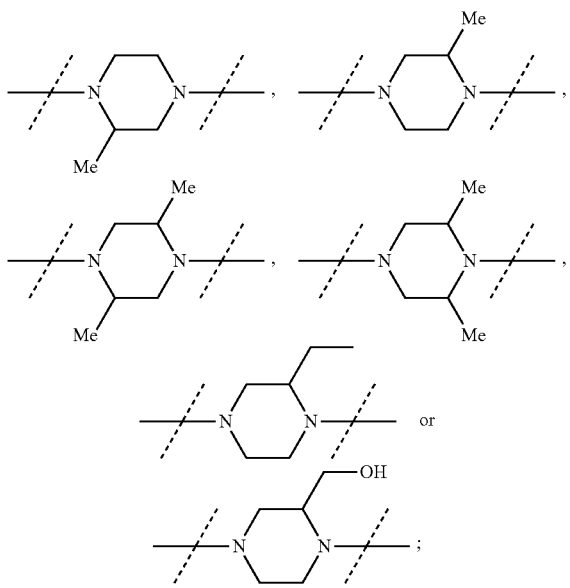

or a pharmaceutically acceptable salt thereof.

2. The compound of claim 1 wherein $R^1$ is hydrogen, fluoro or cyano, or a pharmaceutically acceptable salt thereof.

3. The compound according to claim 2 wherein $R^1$ is fluoro, or a pharmaceutically acceptable salt thereof.

4. The compound according to claim 1 wherein $R^2$ is hydrogen or fluoro, or a pharmaceutically acceptable salt thereof.

5. The compound according to claim 4 wherein $R^2$ is hydrogen, or a pharmaceutically acceptable salt thereof.

6. The compound according to claim 1 wherein $R^3$ is hydrogen, or a pharmaceutically acceptable salt thereof.

7. The compound according to claim 1 wherein $R^4$ is fluoro, chloro, cyano, trifluoromethoxy, trifluoromethyl or difluoromethoxy, or a pharmaceutically acceptable salt thereof.

8. The compound according to claim 7 wherein $R^4$ is fluoro or cyano, or a pharmaceutically acceptable salt thereof.

9. The compound according to claim 1 wherein

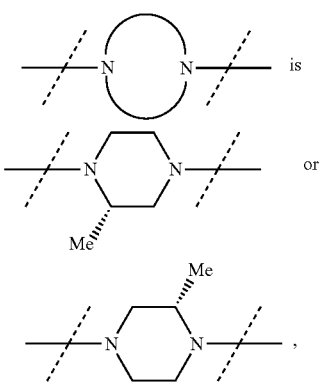

or a pharmaceutically acceptable salt thereof.

10. The compound according to claim 1 which is (S)—N-(4-Fluorophenyl)-4-(4-(4-fluorophenyl)phthalazin-1-yl)-2-methylpiperazine-1-carboxamide, or a pharmaceutically acceptable salt thereof.

11. The compound according to claim 10 which is (S)—N-(4-Fluorophenyl)-4-(4-(4-fluorophenyl)phthalazin-1-yl)-2-methylpiperazine-1-carboxamide hydrochloride.

12. A pharmaceutical composition comprising a compound of the following formula:

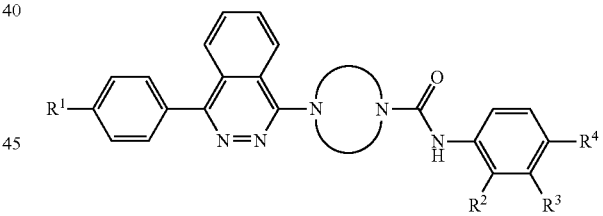

wherein
$R^1$ is hydrogen, fluoro, cyano, trifluoromethyl or methoxy;
$R^2$ is hydrogen, fluoro or trifluoromethyl;
$R^3$ is hydrogen or chloro, provided that at least one of $R^2$ and $R^3$ is hydrogen;
$R^4$ is chloro, fluoro, cyano, trifluoromethyl, difluoromethoxy, methoxy or trifluoromethoxy;

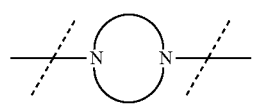

represents a substituted piperazine-1,4-diyl selected from the group consisting of,

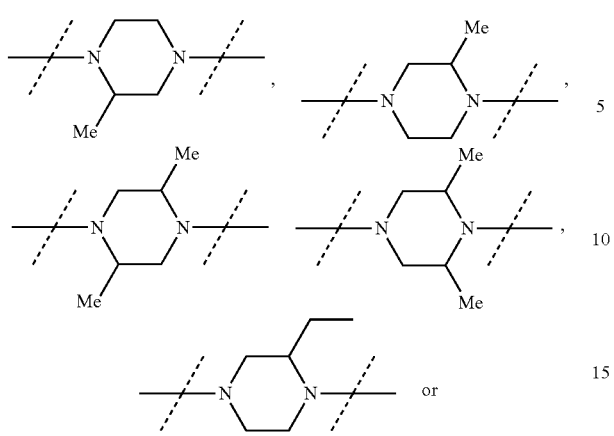,

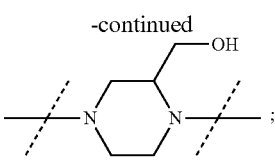

or a pharmaceutically acceptable salt thereof, in combination with a pharmaceutically acceptable carrier, diluent or excipient.

13. A pharmaceutical composition comprising a compound which is (S)—N-(4-Fluorophenyl)-4-(4-(4-fluorophenyl)phthalazin-1-yl) -2-methylpiperazine-1-carboxamide, or a pharmaceutically acceptable salt thereof, in combination with a pharmaceutically acceptable carrier, diluent or excipient.

* * * * *